US012680119B2

(12) United States Patent
Buller et al.

(10) Patent No.: US 12,680,119 B2
(45) Date of Patent: Jul. 14, 2026

(54) METHOD FOR PRODUCING TERTIARY β-HYDROXY-α-AMINO ACIDS

(71) Applicant: Wisconsin Alumni Research Foundation, Madison, WI (US)

(72) Inventors: Andrew Buller, Madison, WI (US); Tyler Doyon, Eau Claire, WI (US); Samantha Bruffy, Madison, WI (US); Anthony Meza, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 547 days.

(21) Appl. No.: 18/351,559

(22) Filed: Jul. 13, 2023

(65) Prior Publication Data

US 2024/0026396 A1 Jan. 25, 2024

Related U.S. Application Data

(60) Provisional application No. 63/388,722, filed on Jul. 13, 2022.

(51) Int. Cl.
*C12P 13/06* (2006.01)
*C12P 13/08* (2006.01)

(52) U.S. Cl.
CPC ............... *C12P 13/06* (2013.01); *C12P 13/08* (2013.01)

(58) Field of Classification Search
None
See application file for complete search history.

(56) References Cited

U.S. PATENT DOCUMENTS

| | | | | |
|---|---|---|---|---|
| 1,824,676 | A | 9/1931 | Mannich | |
| 1,889,678 | A | 11/1932 | Mannich | |
| 2,744,141 | A | 5/1956 | Hayes | |
| 2006/0263861 | A1 | 11/2006 | Nozaki | |
| 2025/0034544 | A1 * | 1/2025 | Alvizo | C12N 9/88 |

OTHER PUBLICATIONS

Bruffy ("Biocatalytic asymmetric aldol addition into unactivated ketones", Nature Chemistry, 2024, 16, 2076-2083). (Year: 2024).*

Altschul, S. F., Gish, W., Miller, W., Myers, E. W., & Lipman, D. J. (1990). Basic local alignment search tool. Journal of molecular biology, 215(3), 403-410.

Doyon, T. J., Kumar, P., Thein, S., Kim, M., Stitgen, A., Grieger, A. M., . . . & Buller, A. R. (2022). Scalable and selective β-hydroxy-α-amino acid synthesis catalyzed by promiscuous l-threonine transaldolase ObiH. ChemBioChem, 23(2), e202100577.

Gibson DG, Young L, Chuang RY, Venter JC, Hutchison CA 3rd, Smith HO (2009). "Enzymatic assembly of DNA molecules up to several hundred kilobases," Nature Methods 6 (5): 343-345.

(Continued)

*Primary Examiner* — Robert J Yamasaki
*Assistant Examiner* — Charles Zoltan Constantine
(74) *Attorney, Agent, or Firm* — Joseph T. Leone; Yanjun Ma; DeWitt LLP

(57) ABSTRACT

A method to make tertiary β-hydroxy α-amino acids. The method includes reacting a ketone substrate and a primary or secondary β-hydroxy α-amino acid with an L-threonine aldolase and/or an L-threonine transaldolase for a time, at a temperature, and at a pH wherein the reaction yields a tertiary β-hydroxy α-amino acid product.

26 Claims, 16 Drawing Sheets

Specification includes a Sequence Listing.

Native, reversible reaction

Previously shown to work with a wide array of R-groups

Claimed here

(56) References Cited

OTHER PUBLICATIONS

Henikoff & Henikoff, Amino acid substitution matrices from protein blocks (1989) Proc. Natl. Acad. Sci. USA 89:10915.
Karlin & Altschul, Applications and statistics for multiple high-scoring segments in molecular sequences, (1993) Proc. Natl. Acad. Sci. USA 90:5873-5787.
Kou, Q.; Wang, T.; Zou, F.; Zhang, S.; Chen, Q.; Yang, Y. "Design, synthesis and biological evaluation of C(4) substituted monobactams as antibacterial agents against multidrug-resistant Gram-negative bacteria," Eur. J. Med. Chem. 2018, 151, 98.
Kumar, P.; Meza, A.; Ellis, J. M.; Carlson, G. A.; Bingman, C. A.; Buller, A. R. L-Threonine transaldolase activity is enabled by a persistent catalytic intermediate, ACS Chem. Biol. 2021, 16, 95.
Li, Z.; Jangra, H.; Chen, Q.; Mayer, P.; Ofial, A. R.; Zipse, H.; Mayr, H., Kinetics and Mechanism of Oxirane Formation by Darzens Condensation of Ketones: Quantification of the Electrophilicities of Ketones , J. Am. Chem. Soc. 2018, 140 (16), 5500.
Needleman & Wunsch, A General Method Applicable to the Search for Similarities in the Amino Acid Sequence of Two Proteins (1970) J. Mol. Biol. 48:443.
Pearson & Lipman, Improved tools for biological sequence comparison, (1988) Proc. Nat'l. Acad. Sci. USA 85:2444.
Schaffer, J. E.; Reck, M. R.; Prasad, N. K.; Wencewicz, T. A., β-Lactone formation during product release from a nonribosomal peptide synthetase Nat. Chem. Biol. 2017, 13 (7), 737.
Scott, T. A.; Heine, D.; Qin, Z.; Wilkinson, B. An L-threonine transaldolase is required for L-threo-β-hydroxy-α-amino acid assembly during obafluorin biosynthesis Nat. Commun. 2017, 8 (May), 15935.
Smith & Waterman. Comparison of Biosequences (1981) Adv. Appl. Math. 2:482.
Xiu et al. (2022) "Multi-enzyme cascade for sustainable synthesis of L-threo-phenylserine by modulating aldehydes inhibition and kinetic/thermodynamic controls," Systems Microbiology and Biomanufacturing 2:705-715.
Xu, L.; Wang, L. C.; and Xu, X. Q.; Lin, J. Characteristics of L-threonine transaldolase for asymmetric synthesis of β-hydroxy-α-amino acids, Catal. Sci. Technol. 2019, 9 (21), 5943.
Xu, L.; Wang, L. C.; Su, B. M.; Xu, X. Q.; Lin, J. Efficient biosynthesis of (2S, 3R)-4-methylsulfonylphenylserine by artificial self-assembly of enzyme complex combined with an intensified acetaldehyde elimination system, Bioorg. Chem. 2021, 110, 104766.

* cited by examiner

Polyoxypeptin
(Anticancer)

Tertiary β-OH
Amino Acids

Chitinopeptin
(Antibacterial)

Resormycin
(Antifungal)

Native, reversible reaction

Previously reported synthetic reactions:

Aldehydes Chiral 2° alcohol sidechain

Claimed here:

**Activated *Ketone* Chiral 3° alcohol sidechain**

EWG = Electron withdrawing group
e.g. -CN; -COOMe; $-CF_3$

| entry | Thr (mM) | ObiH | *Sc*ADH (w/v) | *Cb*FDH (w/v) | d.r. | yield (%) |
|---|---|---|---|---|---|---|
| 1 | 100 | 0.5% | 0.5% | 0.5% | 10:1 | 39% |
| 2 | 100 | 1.0% | 1.0% | 1.0% | 7:1 | 43% |
| 3 | 100 | 1.5% | 1.5% | 1.5% | 5:1 | 43% |
| 4 | 100 | 2.0% | 2.0% | 2.0% | 4:1 | 41% |
| 5 | 100 | 2.0% | 0.5% | 0.5% | 7:2 | 29% |
| 6 | 100 | 0.5% | 2.0% | 0.5% | 14:1 | 53% |
| 7 | 100 | 0.5% | 0.5% | 2.0% | 12:1 | 38% |
| 8 | 100 | 2.0% | 0.5% | 2.0% | 4:1 | 30% |
| 9 | 150 | 0.5% | 2.5% | 0.5% | 17:1 | 67% |
| 10 | 150 | 5 μM | 2.5% | 0.5% | 14:1 | 73% |

METHOD FOR PRODUCING TERTIARY β-HYDROXY-α-AMINO ACIDS

CROSS-REFERENCE TO RELATED APPLICATIONS

Priority is hereby claimed to provisional application Ser. No. 63/388,722, filed Jul. 13, 2022, which is incorporated herein by reference.

FEDERAL FUNDING STATEMENT

This invention was made with government support under GM 137417 awarded by the National Institutes of Health. The government has certain rights in the invention.

SEQUENCE LISTING

The instant application contains a Sequence Listing which has been submitted in an XML file with the USPTO and is incorporated herein by reference in its entirety. The Sequence Listing was created on Apr. 5, 2023, is named "SEQ_LIST-P220362US02.xml," and is 14,199 bytes in size.

BACKGROUND

Modifying the structure of amino acids is an important strategy for tuning the properties of bioactive compounds. Hydroxylating the β-position of amino acids to produce a secondary alcohol is a common modification. There are many conventional synthetic routes to make such amino acids. However, there are very few strategies, synthetic or biological, that are capable of producing α-amino acids that have a tertiary alcohol at the ii position. Examples of bioactive compounds bearing tertiary β-hydroxy amino acid sidechains are shown in FIG. 1. Disclosed herein is a non-natural, enzymatic method for producing tertiary β-hydroxy α-amino acids.

In the patent literature, see, for example, U.S. Pat. No. 2,744,141, issued May 1, 1956, to Hayes and Drake. As noted there, in the past it was conventional to make saturated, linear amino alcohols from the corresponding amino aldehyde using the Mannich reaction. See also U.S. Pat. Nos. 1,824,676 and 1,889,678. However, reducing the aldehyde reactant to the corresponding beta-hydroxy amino acid via this route is quite cumbersome. The Hayes and Drake route yields an aliphatic, saturated secondary or tertiary β-hydroxy α-amino acid by reducing the corresponding amino aldehyde in isopropanol using aluminum isopropoxide as the reductant.

More recently, see U.S. Pat. Appl. Publ. US 2006/0263861, published Nov. 23, 2006, to Nozaki et al. This reference describes a method for producing optically active β hydroxy amino acids reacting a D-α-amino acid and 5,10-methylene tetrahydrofolic acid in the presence of an enzyme derived from a microorganism belonging to the genera *Paracoccus, Aminobacter*, or *Ensifer.*

The native reaction of L-threonine transaldolases ("L-T-transA") such as ObiH is to catalyze the formation of non-standard amino acids ("nsAA") having a secondary alcohol. See, for example, Scott, T. A.; Heine, D.; Qin, Z.; Wilkinson, B. *Nat. Commun.* 2017, 8 (May), 1 and Schaffer, J. E.; Reck, M. R.; Prasad, N. K.; Wencewicz, T. A. *Nat. Chem. Biol.* 2017, 13 (7), 737. ObiH has been used to produce a variety of β-hydroxy amino acids via reactions with aldehyde substrates. See Doyon, T. J.; Kumar, P.; Thein, S.; Kim, M.; Stitgen, A.; Grieger, A. M.; Madigan, C.; Willoughby, P. H.; Buller, A. R.; Thien, S.; Kim, M.; Stitgen, A.; Greiger, A.; Madigan, C.; Willoughby, P. H.; Buller, A. R. *ChemBioChem* 2022, 23 (2), 1; Kumar, P.; Meza, A.; Ellis, J. M.; Carlson, G. A.; Bingman, C. A.; Buller, A. R. *ACS Chem. Biol.* 2021, 16, 95; Xu, L.; Wang, L. C.; and Xu, X. Q.; Lin, *J. Catal. Sci. Technol.* 2019, 9 (21), 5943.

It has also been previously shown that an L-T-transA can be coupled with a dehydrogenase to improve yield of reactions with aldehyde substrates. Xu, L.; Wang, L. C.; Su, B. M.; Xu, X. Q.; Lin, *J. Bioorg. Chem.* 2021, 110, 104766.

Reactions with ketone electrophiles are significantly more challenging than with aldehydes. See, for example, Li, Z.; Jangra, H.; Chen, Q.; Mayer, P.; Ofial, A. R.; Zipse, H.; Mayr, H. *J. Am. Chem. Soc.* 2018, 140 (16), 5500. Notably, amino acids with tertiary alcohol sidechains are cumbersome to produce through traditional methodology. See FIG. 2 and Kou, Q.; Wang, T.; Zou, F.; Zhang, S.; Chen, Q.; Yang, Y. "Design, synthesis and biological evaluation of C(4) substituted monobactams as antibacterial agents against multidrug-resistant Gram-negative bacteria," *Eur. J. Med. Chem.* 2018, 151, 98.

Thus, there remains a long-felt and unmet need for a simplified, streamlined method to make tertiary β-hydroxy α-amino acids cheaply and in high yield.

SUMMARY

Disclosed herein is a method to make an amino acid having a tertiary alcohol sidechain, wherein the method comprises reacting a pyridoxal-phosphate (PLP)-dependent enzyme with a ketone substrate and a primary or secondary β-hydroxy amino acid for a time, and at a temperature, wherein the reaction yields the desired amino acid with a tertiary alcohol sidechain. The preferred enzymes for use in the method are selected from the group consisting of L-threonine aldolases ("L-TA," EC 4.1.2.5;) and L-threonine transaldolases ("L-T-transA," no general EC number is recognized, but EC 2.2.1.4 is representative; ObiH is a preferred L-T-transA). Natively, all known L-TA and L-T-transA enzymes react with aldehydes and yield chiral secondary alcohol sidechains. No members have been reported previously to react with a ketone, which is an historically distinct chemical challenge. There has been no previous report of using L-TA or L-T-TransA enzymes to yield amino acids having a tertiary alcohol sidechain.

Thus, disclosed herein is a method to make amino acid having a tertiary alcohol sidechain, the method comprising reacting a pyridoxal-phosphate (PLP)-dependent enzyme selected from the group consisting of an L-threonine aldolase, an L-threonine transaldolase, or a combination thereof, with a ketone substrate and a primary or secondary β-hydroxy α-amino acid for a time, at a temperature, and at a pH wherein the reaction yields a tertiary β-hydroxy α-amino acid. Preferred primary or secondary β-hydroxy α-amino acid reactants include serine, threonine, and 3-phenyl serine.

In one version of the method, the PLP-dependent enzyme is an L-threonine aldolase.

In another version of the method, the PLP-dependent enzyme is an L-threonine transaldolase. A preferred PLP-dependent L-threonine transaldolase enzyme for use in the method is ObiH.

The reaction conditions are very tolerant, with preferred reaction times generally running from about 1 hour to about 12 hours, preferred temperatures from about 30° C. to about 50° C., and preferred pH from about 6 to about 8. These are preferred ranges. Values above and below these stated ranges are explicitly within the scope of the attached claims.

The method may further comprise reacting the PLP-dependent enzyme and the ketone substrate in the presence of a reducing system. The reducing system is dimensioned, configured, and functions, to reduce aldehyde by-products formed in the reaction. In one version of the method, the method further comprises the step of reducing the aldehyde by products by contacting them with an alcohol dehydrogenase in the presence of NAD(P)H, wherein the alcohol dehydrogenase reduces at least a portion of the aldehyde by-products, and NAD(P)+ is generated. The reaction may further comprise regenerating NAD(P)H from the NAD(P)+ by contacting the NAD(P)+ with a formate dehydrogenase. This can be accomplished by contacting the NAD(P)+ with a formate dehydrogenase.

In a preferred implementation of the method, the ketone substrate further comprises an electron-withdrawing group.

The method will work with any secondary β-hydroxy α-amino acid as a co-reactant.

The objects and advantages of the disclosure will appear more fully from the following detailed description of the preferred embodiment of the disclosure made in conjunction with the accompanying drawings.

DETAILED DESCRIPTION

Abbreviations and Definitions

"ADH" means "alcohol dehydrogenase" from any source.

"BmGDH means glucose dehydrogenase from *Bacillus megaterium*. See, for example, Xiu et al. (2022) "Multi-enzyme cascade for sustainable synthesis of L-threo-phenylserine by modulating aldehydes inhibition and kinetic/thermodynamic controls," *Systems Microbiology and Biomanufacturing* 2:705-715.

"EWG" means "electron-withdrawing group." An electron-withdrawing group is an atom or functional group capable of withdrawing electron density from a conjugated system. Electron density can be withdrawn through a bonds (inductive) or through it bonds (resonance). Some functional groups are donating groups by one mechanism and withdrawing groups through the other mechanism. Exemplary electron withdrawing groups include, but are not limited to, halo, haloalkyl, $—NH_3^+$, $—NO_2$, $—CH—CH_2$, —CN, $—SO_3H$, —C(=O)OH, —C(=O)H, —C(=O)R, —C(=O)OR, $—NR_3^+$, where R is alkyl, such as lower alkyl (e.g., methyl, ethyl, etc.).

"FDH" means "formate dehydrogenase" from any source. "CbFDH" means a formate dehydrogenase from *Candida boidinii*.

Figure 1:
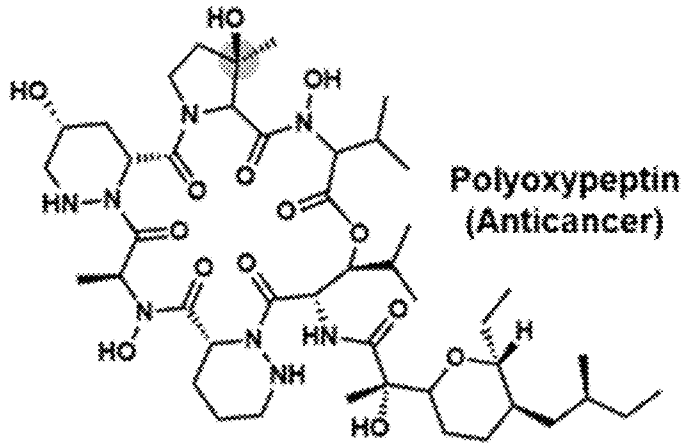
FIG. 1 depicts examples of bioactive compounds bearing tertiary β-hydroxy amino acid sidechains. The panel in the upper-right corner depicts the conventional Greek letter identifiers employed—the α-carbon being the carbon atom bearing the amino moiety.
Figure 1:
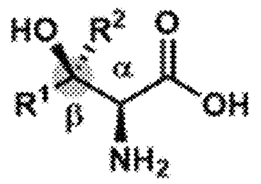
Figure 1:
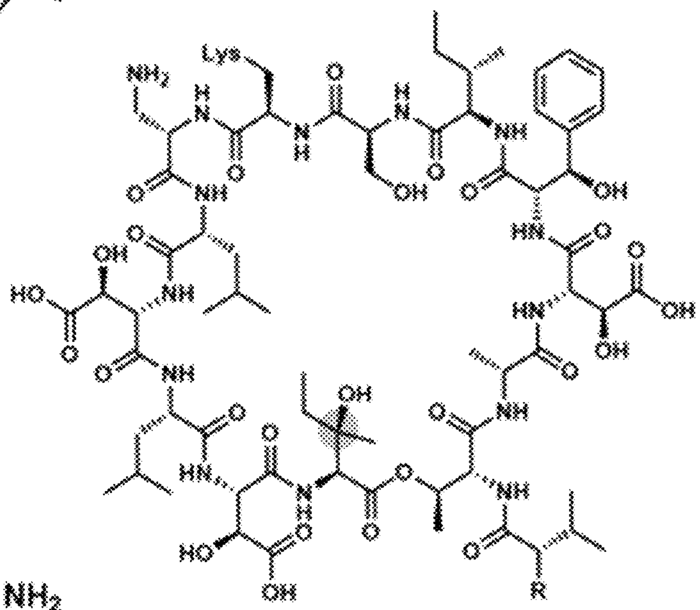
Figure 1:
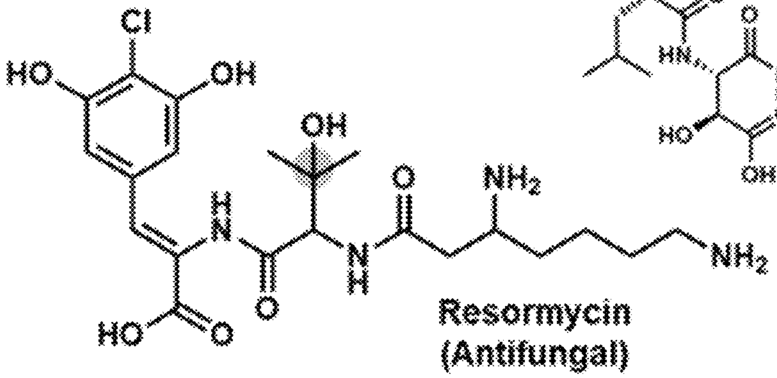
Figure 2:
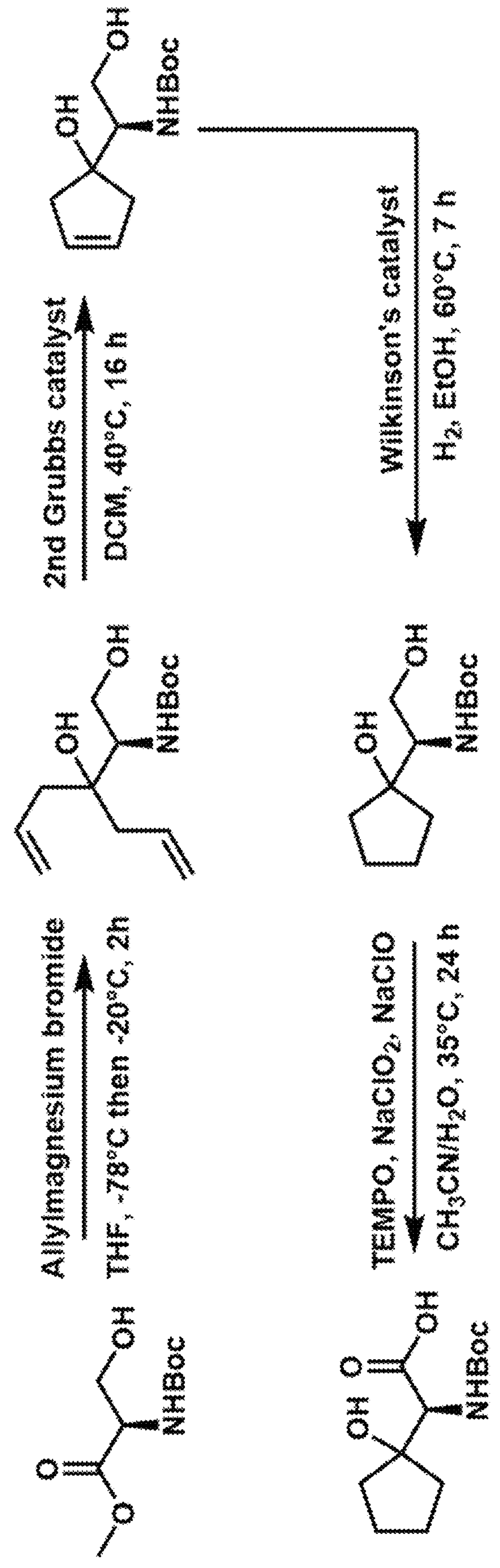
FIG. 2 depicts a prior art for producing tertiary alcohol-containing non-standard amino acids. See Kou, Q.; Wang, T.; Zou, F.; Zhang, S.; Chen, Q.; Yang, Y. "Design, synthesis and biological evaluation of C(4) substituted monobactams as antibacterial agents against multidrug-resistant Gram-negative bacteria," Eur. J. Med. Chem. 2018, 151, 98.
Figure 3:
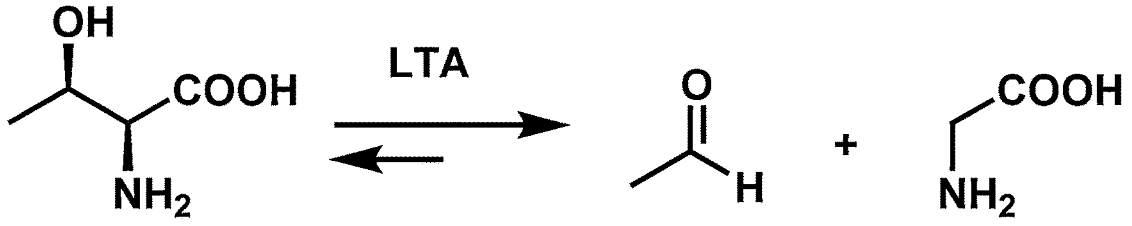
FIG. 3 depicts a generic reaction scheme according to the disclosed method in which an L-TA enzyme (EC 4.1.2.5) is used to synthesize amino acids containing tertiary alcohol sidechains.
Figure 3:
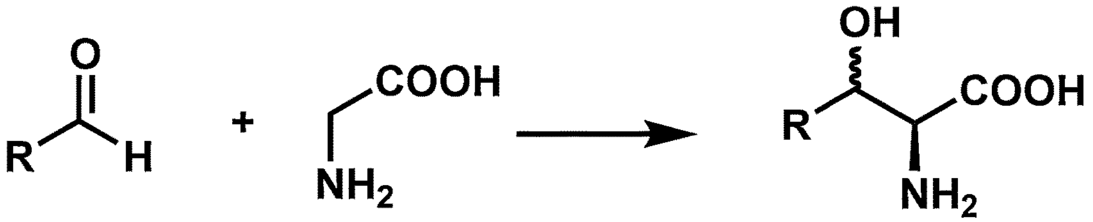
Figure 3:
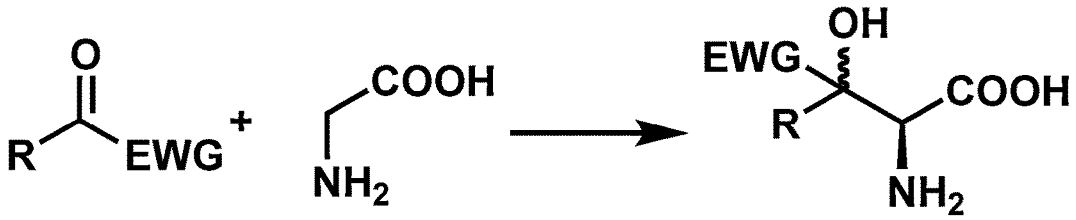

The term "L-threonine aldolase" ("L-TA") is used generically herein to refer to any enzyme falling within enzyme classification EC 4.1.2.5. In its native milieu, L-TAs catalyze the cleavage of L-threonine to yield acetaldehyde and glycine. See the top panel of FIG. 3.

The term "L-threonine transaldolase" ("L-T-transA") is used generically herein to refer to any enzyme that in its native milieu catalyzes the formation of secondary β-hydroxy α-amino acids. See the middle panel of FIG. 3.

"NAD(P)+" and "NAD(P)H" nicotinamide adenine dinucleotide phosphate and its reduced form, respectively.

"nsAA" means "non-standard amino acid."

"ObiH" refers to an L-threonine transaldolase isolated from *Pseudomonas fluorescens*. In its native milieu, ObiH is involved in the biosynthesis of the beta-lactam antibiotic obafluorin:

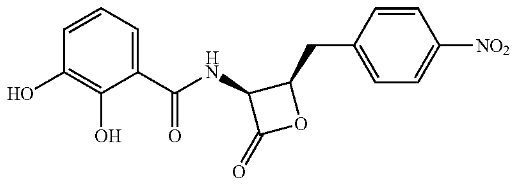 [SMILES: O=C(N[C@@H]1C(=O)O[C@@H]1Cc1ccc([N+](=O)[O-])cc1)c1cccc(O)c1O]

"PLP" refers to the co-enzyme "pyridoxal-5'-phosphate" (also known as Vitamin B6):

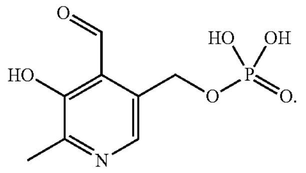 [SMILES: Cc1ncc(COP(=O)(O)O)c(C=O)c1O]

"RS" means "reducing system."

"ScADH" means alcohol dehydrogenase from *Saccharomyces cerevisiae*"

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Nucleic acid or protein sequences of any known gene, including the genes or proteins described herein, can be determined by searching any sequence databases known in the art using the gene name or accession number as a search term. Common sequence databases include GenBank (www.ncbi.nlm.nih.gov), ExPASy (expasy.org), KEGG (www.genome.jp), among others.

Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the genes or proteins described herein include genes or proteins having at least about 30%, 35%, 40%, 45%, 50%, 55%, 60%, 65%, 70%, 75%, 80%, 85%, 90%, 95%, or 99% identity to the genes or proteins described herein.

Methods for determining sequence similarity percentages (e.g., BLASTP and BLASTN using default parameters) are described herein and are generally available. The homologous proteins should demonstrate comparable activities and (if an enzyme) participate in the same or analogous pathways. Homologs include orthologs and paralogs. "Orthologs" are genes and products thereof in different species that evolved from a common ancestral gene by speciation. Normally, orthologs retain the same or similar function in the course of evolution. Paralogs are genes and products thereof related by duplication within a genome. As used herein, "orthologs" and "paralogs" are included in the term "homologs."

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence is a nucleic acid or amino acid sequence corresponding to the genes or proteins described herein.

Optimal alignment of sequences for comparison can be conducted, e.g., by the local homology algorithm of Smith & Waterman (1981) *Adv. Appl. Math.* 2:482, by the homology alignment algorithm of Needleman & Wunsch (1970) *J. Mol. Biol.* 48:443, by the search for similarity method of Pearson & Lipman (1988) *Proc. Nat'l. Acad. Sci.* USA 85:2444, by computerized implementations of these algorithms (GAP, BESTFTT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al. (1990) *J. Mol. Biol.* 215:403-410. Software for performing BLAST analyses is publicly available through the National Center for Biotechnology Information. This algorithm involves first identifying high scoring sequence pairs (HSPs) by identifying short words of length "W" in the query sequence, which either match or satisfy some positive-valued threshold score "T" when aligned with a word of the same length in a database sequence. "T" is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (reward score for a pair of matching residues; always >0) and "N" (penalty score for mismatching residues; always <0). For amino acid sequences, a scoring matrix is used to calculate the cumulative score. Extension of the word hits in each direction are halted when: the cumulative alignment score falls off by the quantity "X" from its maximum achieved value; the cumulative score goes to zero or below, due to the accumulation of one or more negative-scoring residue alignments; or the end of either sequence is reached. The BLAST algorithm parameters "W," "T," and "X" determine the sensitivity and speed of the alignment. The BLASTN program (for nucleotide sequences) uses as defaults a wordlength ("W") of 11, an expectation ("E") of 10, a cutoff of 100, "M"=5, "N"=−4, and a comparison of both strands. For amino acid sequences, the BLASTP program uses as defaults a wordlength ("W") of 3, an expectation ("E") of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The term "alkyl" refers to a branched or unbranched carbon chain having, for example, about 1-20 carbon atoms, and often 1-12, 1-10, 1-8, 1-6, or 1-4 carbons. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2 pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated in certain embodiments. As such, the recitation of an alkyl group optionally includes both alkenyl and alkynyl groups. The alkyl can be a monovalent hydrocarbon radical, as described and exemplified above, or it can be a divalent hydrocarbon radical (i.e., an alkylene). In some embodiments, certain alkyl groups can be excluded from a definition. For example, in some embodiments, methyl, ethyl, propyl, butyl, or a combination thereof, can be excluded from a specific definition of alkyl in an embodiment.

The term "cycloalkyl" refers to cyclic alkyl groups of, for example, 3 to about 12, 3 to about 10, 3 to about 8, about 4 to about 8, or 5-6, carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

As used herein, "aryl" refers to an aromatic hydrocarbon group derived from the removal of one hydrogen atom from a single carbon atom of a parent aromatic ring system. The radical attachment site can be at a saturated or unsaturated carbon atom of the parent ring system. The aryl group can have from 6 to about 20 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heteroaryl" refers to a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described in the definition of "substituted". Typical heteroaryl groups contain 2-20 carbon atoms in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or —($C_1$-$C_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "substituted" indicates that one or more hydrogen atoms on the group indicated in the expression using "substituted" is replaced with a "substituent." The number referred to by "one or more" can be apparent from the moiety one which the substituents reside. For example, "one or more" can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups include, i., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl(alkyl)amine, and cyano. Additionally, suitable substituent groups can be, e.g., —X, —R, —O—, —OR, —SR, —S—, —$NR_2$, —$NR_3$, ═NR, —$CX_3$, —CN, —OCN, —SCN, —N═C═O, —NCS, —NO, —$NO_2$, $N_2$, —$N_3$, —NC(═O)R, —C(═O)R, —C(═O)NRR, —S(═O)$_2$O—, —S(═O)$_2$OH, —S(═O)$_2$R, —OS(═O)$_2$OR, —S(═O)$_2$NR, —S(C)R, —OP(═O)O$_2$RR, —P(═O)O$_2$RR, —P(═)(O—)$_2$, —P(═O)(OH)$_2$, —C(═O)R, —C(═O)X, —C(S)R, —C(O)OR, —C(O)O—, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (═O) or thioxo (═S), or the like, then two hydrogen atoms on the substituted atom are replaced.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the disclosed method shall include the corresponding plural characteristic or limitation, and vice-versa, unless otherwise specified or clearly implied to the contrary by the context in which the reference is made. The indefinite articles "a" and "an" mean "one or more."

All combinations of method steps disclosed herein can be performed in any order, unless otherwise specified or clearly implied to the contrary by the context in which the referenced combination is made.

The method disclosed herein can comprise, consist of, or consist essentially of the essential elements and steps described herein, as well as any additional or optional ingredients, components, or limitations described herein or otherwise useful in synthetic/enzymatic organic chemistry. The method disclosed herein may be practiced in the absence of any element or step which is not specifically disclosed herein.

Description of the Method

Newly developed and disclosed herein is a method of reacting an L-TA enzyme (EC 4.1.2.5) and/or an L-T-transA enzyme with a ketone substrate to yield a tertiary β-hydroxy α-amino acid product. The basic approach is illustrated in the bottom panel of FIG. 3, wherein "EWG" is an electron-withdrawing group of any description (for example, a halogen, a halo-alkyl group, a cyanate group, and alkyl carboxylate group, and the like; see the definition of EWG hereinabove). As noted above, the core of the method is to react a pyridoxal-phosphate (PLP)-dependent enzyme, either a L-threonine aldolase (L-TA; EC 4.1.2.5) or a L-threonine transaldolase, (such as C-His-TmLTA (SEQ ID NO: 1) or ObiH (SEQ ID NO: 3), respectively) with a ketone substrate and in the presence of an amino acid (glycine is shown in the bottom panel of FIG. 3) to produce an amino acid with a tertiary alcohol sidechain. It is much preferred, but not required, that the ketone substrate includes an EWG to speed the reaction. The EWG functions to activate the ketone group itself, thereby accelerating the reaction. The reaction functions with unactivated ketones, but yields are quite small without a strong driving force. This is because the reaction is reversible and subject to thermodynamic limitations. Thus, while including an EWG in the ketone substrate is not strictly required, it is strongly preferred. The reaction is very flexible in that the required enzyme(s) function to catalyze the reaction in the form of whole cells, lysates, or purified enzyme.

Figure 4:
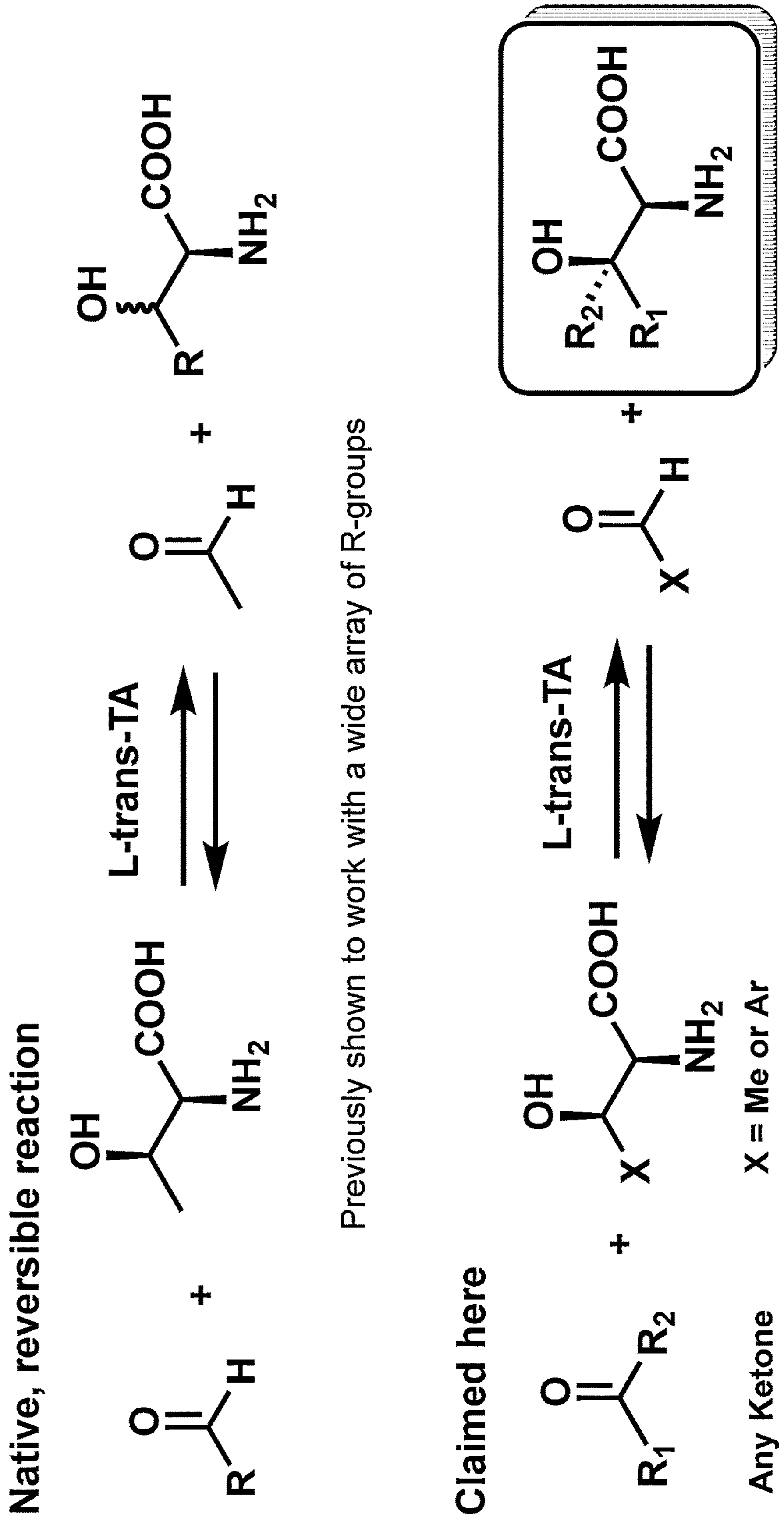
FIG. 4 depicts a generic reaction scheme according to the disclosed method in which an L-T-transA enzyme is used to synthesize amino acids containing tertiary alcohol sidechains.

As shown in FIG. 4, the reaction may also be conducted using an L-T-transA enzyme (such as, but not limited to, ObiH). Here, the L-T-transA catalyzes the formation of C—C bond with threonine to yield an amino acid having a tertiary β-hydroxy sidechain. See FIG. 4, bottom panel. The native, reversible reaction of the L-T-transA enzyme is shown in FIG. 4, top panel. The bottom panel of FIG. 4 illustrates an exemplary implementation of the present method in which a ketone (any ketone) is reacted with a secondary β-hydroxy aryl serine or a secondary β-hydroxy alkyl serine to yield a tertiary β-hydroxy α-amino acid. An aldehyde is formed as a by-product.

Yield of the reaction is improved by coupling the L-T-transA reaction with an appropriate alcohol dehydrogenase (ADH), that uses NAD(P)H to reduce the aldehyde byproduct. This provides increased thermodynamic driving force to the forward reaction and significantly enhances yields.

Figure 5:
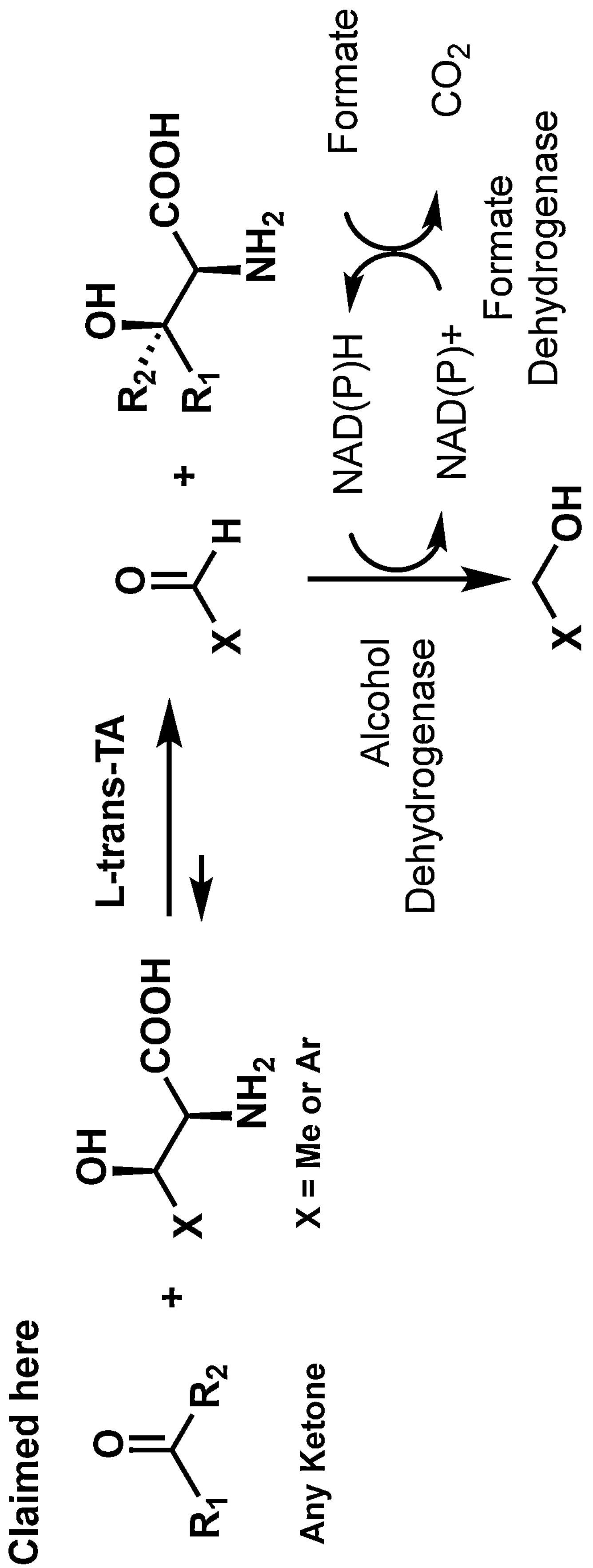
FIG. 5 depicts a cascade reaction according to the present method. The reaction overcomes the well-known thermodynamic limitations encountered when using ketone substrates.

Yield of the reaction is further improved by using a co-factor regeneration reaction that replenishes the NAD(P)+ that is formed when NAD(P)H reduces the aldehyde. That is, in reducing the aldehyde, the NAD(P)H is oxidized to NAD(P)+. Regenerating the NAD(P)H provides still greater thermodynamic driving force for the forward reaction. This is shown in FIG. 5. Across the top of FIG. 5 is shown the same reaction as in the bottom panel of FIG. 4. In the lower-right section of FIG. 5 is shown a cascading co-factor regeneration reaction that regenerates the NAD(P)H to provide additional thermodynamic driving force for the forward reaction shown at the top of FIG. 5. Here, as noted above, an ADH and NAD(P)H are used to reduce the aldehyde by-product of the forward L-T-transA reaction, thereby generating an alcohol and NAD(P)+. As shown in the bottom-right of FIG. 5, a formate dehydrogenase enzyme is used to regenerate the NAD(P)H. In this fashion, the aldehyde by-product is continuously removed by the action of ADH, and the NAD(P)H reductant is regenerated by the action of the formate dehydrogenase. The result is a massive increase in thermodynamic driving force to the forward reaction. Yields are thus increased accordingly.

Figure 6:
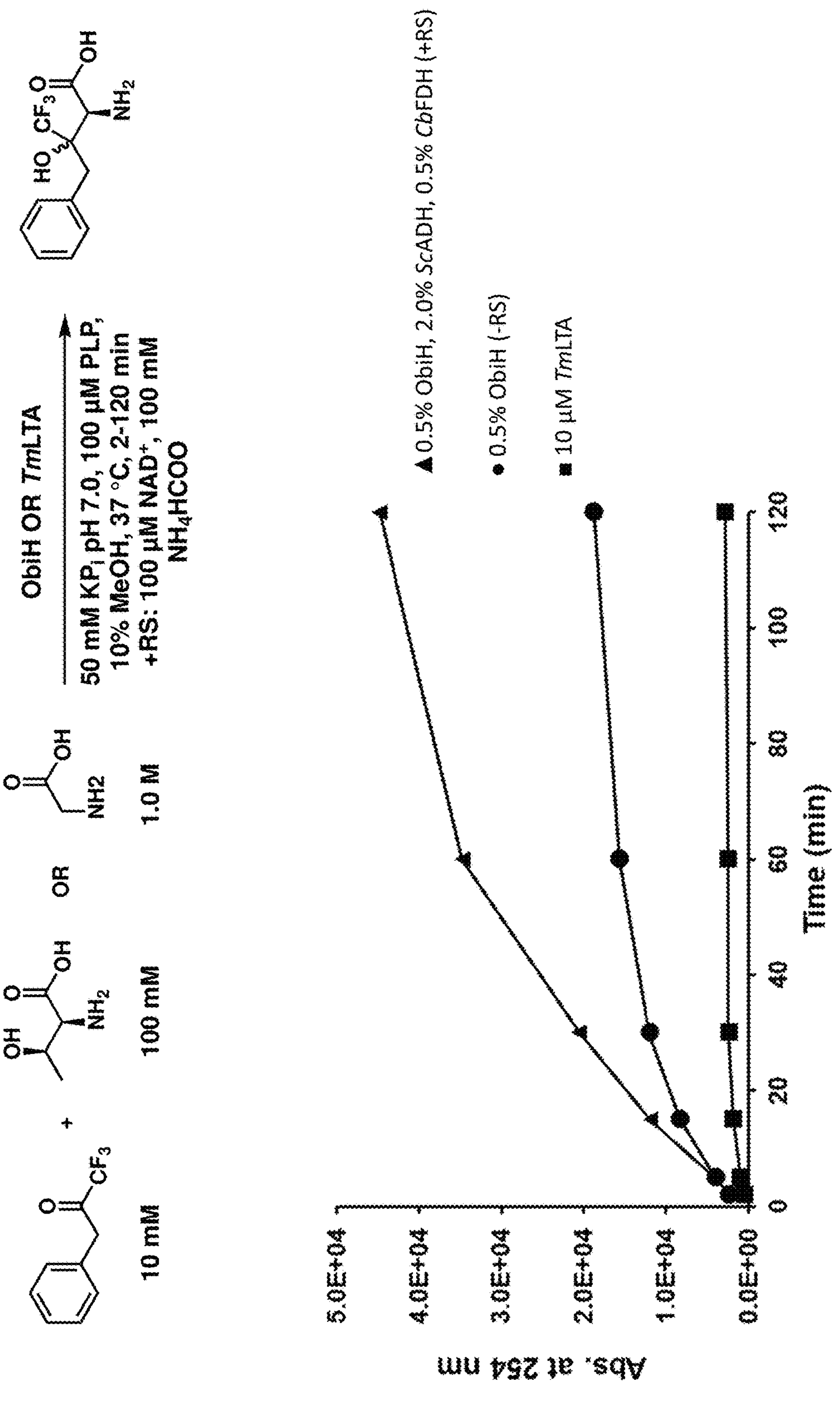
FIG. 6 shows an exemplary reaction of TmLTA and ObiH with an activated, trifluoromethylketone substrate. The time course shows product formation over time. L-TA (square, 1.0 M Gly) produces the least product, corresponding to <10% yield. ObiH forms significantly more product (circle, 100 mM Thr) than TmLTA; that activity is increased further by adding a reducing system (triangle, 100 mM Thr) to provide a thermodynamic driving force.

The results of an exemplary implementation of the method are shown in FIG. 6. As shown across the top of the figure, 10 mM of benzyl-trifluoromethyl ketone were reacted with either threonine or glycine, in the presence of 0.5% ObiH (a L-T-transA enzyme) or TmLTA (L-TA enzyme), in the presence of KPi buffer (pH 7), PLP, 10% v/v methanol ("MeOH"), 0.1 mM NAD*, and 100 mM ammonium formate, at 37° C., and for times ranging from 2 minutes to 120 minutes. The graph shows the formation of the tertiary β-hydroxy α-amino acid product over time. As shown by the top trace, the yield is greatly improved by including the alcohol dehydrogenase/formate dehydrogenase cascade reaction. The middle trace shows the yield over time without the alcohol dehydrogenase/formate dehydrogenase cascade reaction. The bottom trace shows a very small yield when only 10 μM L-TA enzyme is used. LTA (bottom trace, 1.0 M Gly) produces the least product, corresponding to <10% yield. ObiH forms significantly more product (middle trace, 100 mM Thr) than TmLTA.

That activity is increased further by adding the alcohol dehydrogenase/formate dehydrogenase cascade reaction to provide additional thermodynamic driving force.

Figure 7:
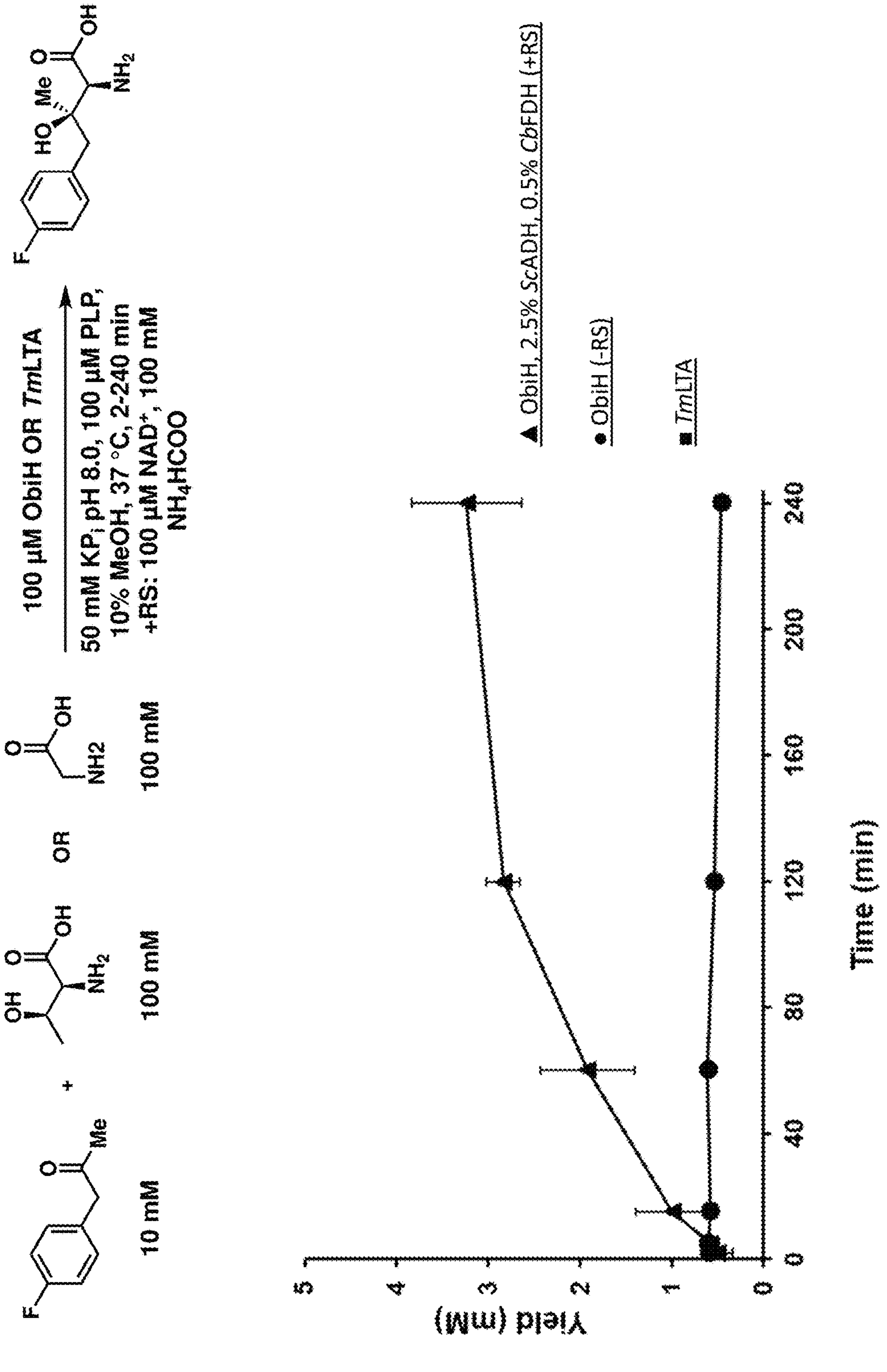
FIG. 7 depicts an exemplary reaction of TmLTA and ObiH with a non-activated, a phenyl acetone substrate. No product was observed with L-TA under these conditions (100 mM Gly). ObiH yields detectable product (bottom trace, 100 mM Thr). A major enhancement in yield is observed by adding a reducing system (top trace, 100 mM Thr) to provide a thermodynamic driving force.

FIG. 7 depicts an exemplary implementation of the method using ObiH or TmLTA without the alcohol dehydrogenase/formate dehydrogenase cascade reaction and without an activated ketone substrate. The substrate was 4-fluorobenzyl methyl ketone and the amino acid was again threonine or glycine. The remaining reaction conditions were as noted above for FIG. 6. Yields were significantly higher for ObiH than for TmLTA. This indicates that the thermodynamics of the L-T-transA-catalyzed reaction (ObiH) are much more favorable than the thermodynamics of the L-TA catalyzed reaction (TmLTA). Under these conditions, the unassisted reaction with TmLTA did not yield any observable product. The ObiH catalyzed reaction did yield product, even with an unactivated ketone and without the alcohol dehydrogenase/formate dehydrogenase cascade reaction (bottom trace). The best yield was realized using an L-T-transA (ObiH) as the enzyme and including in the reaction the alcohol dehydrogenase/formate dehydrogenase cascade reaction (top trace).

Table 1 below presents a comparison of the yields of an exemplary ObiH-catalyzed reaction, with and without the alcohol dehydrogenase/formate dehydrogenase cascade reaction.

TABLE 1

Comparison of ObiH alone to ObiH with acetaldehyde reductase system

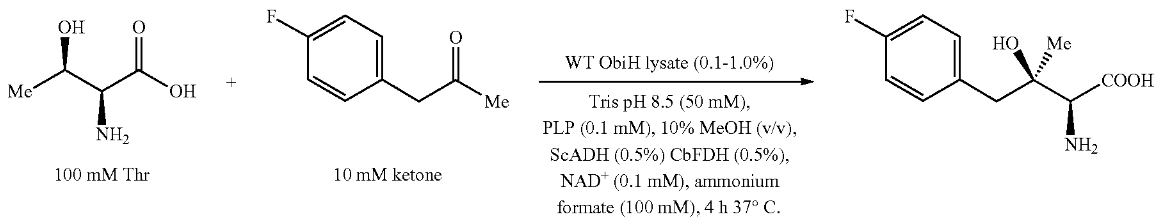 [SMILES: C[C@@H](O)[C@H](N)C(=O)O ; CC(=O)Cc1ccc(F)cc1 ; C[C@@](O)(Cc1ccc(F)cc1)[C@H](N)C(=O)O]

| Entry | ObiH lysate concentration (% w/v) | Reduction system | Product yield (%) |
|---|---|---|---|
| 1 | 0.1% (1 mg/mL) | None | 4% |
| 2 | 0.5% (5 mg/mL) | None | 3% |
| 3 | 1.0% (10 mg/mL) | None | 1% |
| 4 | 0.5% (5 mg/mL) | 0.5% CbFDH + ScADH | 24% |

The data shows that yield is not improved simply by adding a higher concentration of the L-TA or L-T-transA enzyme; see the first two entries in Table 1. Entry 1 used 1 mg/mL ObiH lysate and yield was 4%. Entry 2 used 5 mg/mL ObiH lysate and product yield dropped to 3%. All other reaction conditions were the same.

Further efforts to optimize yields resulted in the data shown in Table 2. Here, the concentrations of Thr, ObiH, ScADH, and CbFDH were varied. Entries 10 (73%), 9 (67%), and 6 (53%) had the best yields. The abbreviation "d.r." stands for "diastereomeric ratio" of the diastereomer shown in the header of Table 2.

TABLE 2

Yield Optimization

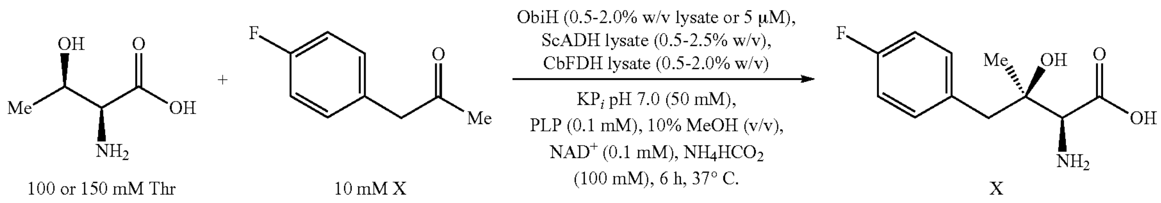

| entry | Thr (mM) | ObiH | ScADH (w/v) | CbFDH (w/v) | d.r. | yield (%) |
|---|---|---|---|---|---|---|
| 1 | 100 | 0.5% | 0.5% | 0.5% | 10:1 | 39% |
| 2 | 100 | 1.0% | 1.0% | 1.0% | 7:1 | 43% |
| 3 | 100 | 1.5% | 1.5% | 1.5% | 5:1 | 43% |
| 4 | 100 | 2.0% | 2.0% | 2.0% | 4:1 | 41% |
| 5 | 100 | 2.0% | 0.5% | 0.5% | 7:2 | 29% |

TABLE 2-continued

Yield Optimization

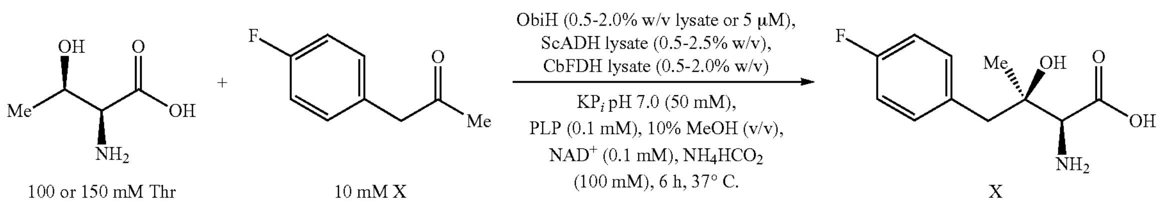

100 or 150 mM Thr     10 mM X     X

| entry | Thr (mM) | ObiH | ScADH (w/v) | CbFDH (w/v) | d.r. | yield (%) |
|---|---|---|---|---|---|---|
| 6 | 100 | 0.5% | 2.0% | 0.5% | 14:1 | 53% |
| 7 | 100 | 0.5% | 0.5% | 2.0% | 12:1 | 38% |
| 8 | 100 | 2.0% | 0.5% | 2.0% | 4:1 | 30% |
| 9 | 150 | 0.5% | 2.5% | 0.5% | 17:1 | 67% |
| 10 | 150 | 5 μM | 2.5% | 0.5% | 14:1 | 73% |

Figure 8:
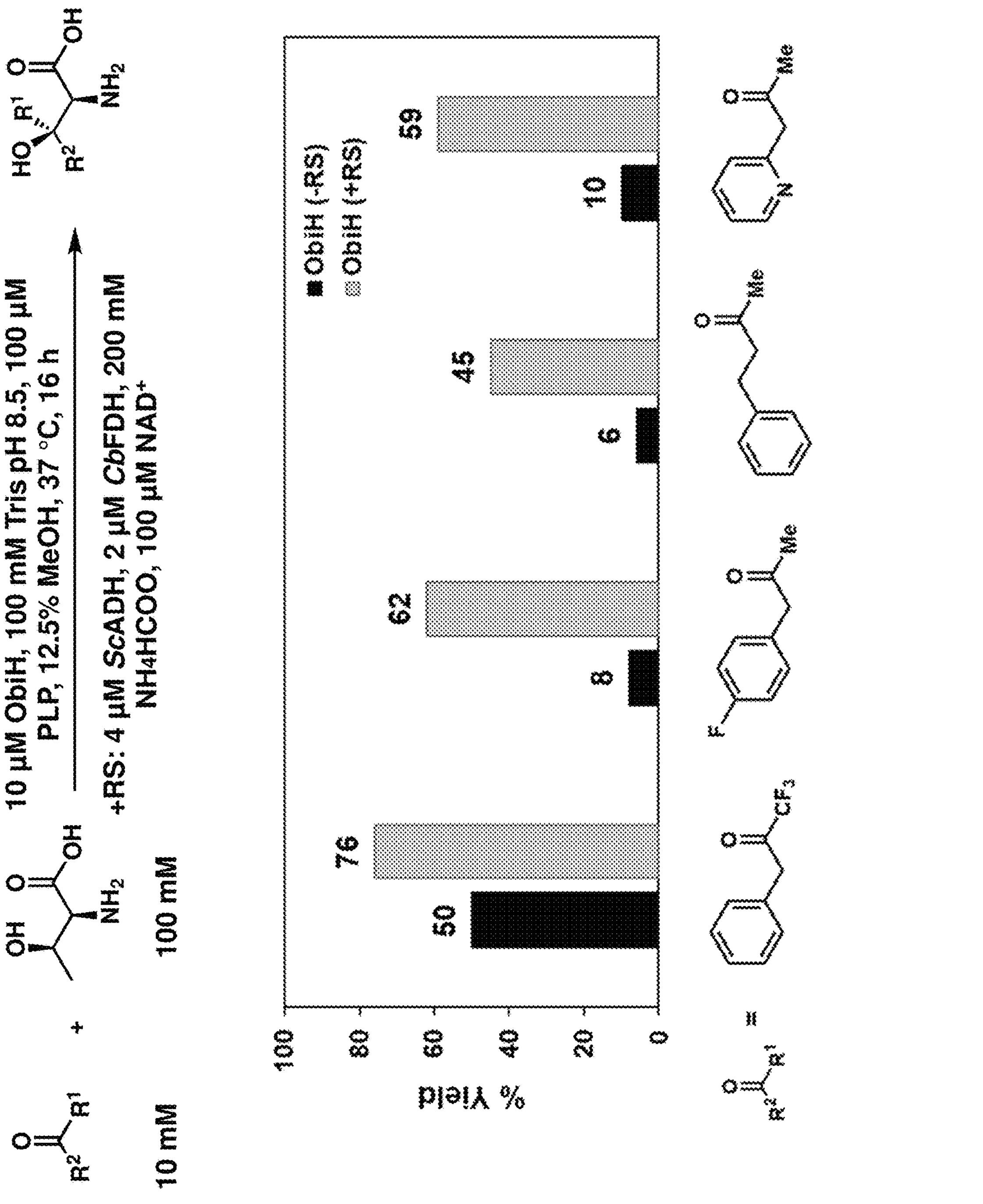
FIG. 8 depicts the increased product yields when using a reducing system in the disclosed method. As shown in the histogram, a reduction system provides a significant increase in activity for diverse ketone substrates.

FIG. 8 shows the marked improvement in yield when an L-T-transA enzyme is used in conjunction with the alcohol dehydrogenase/formate dehydrogenase cascade reaction (which is referred to as the "reduction system" in FIG. 8). The histogram clearly shows that the reduction system provides an increase in activity for diverse ketone substrates. The ketone substrates tested, from left to right in FIG. 8, were benzyl trifluoromethyl ketone, 4-fluorbenzyl methyl ketone, 2-phenyl-methyl methyl ketone, and 2-pyridinyl methyl ketone. Across the board, the yield was vastly improved by using the alcohol dehydrogenase/formate dehydrogenase cascade reaction.

Figure 9:
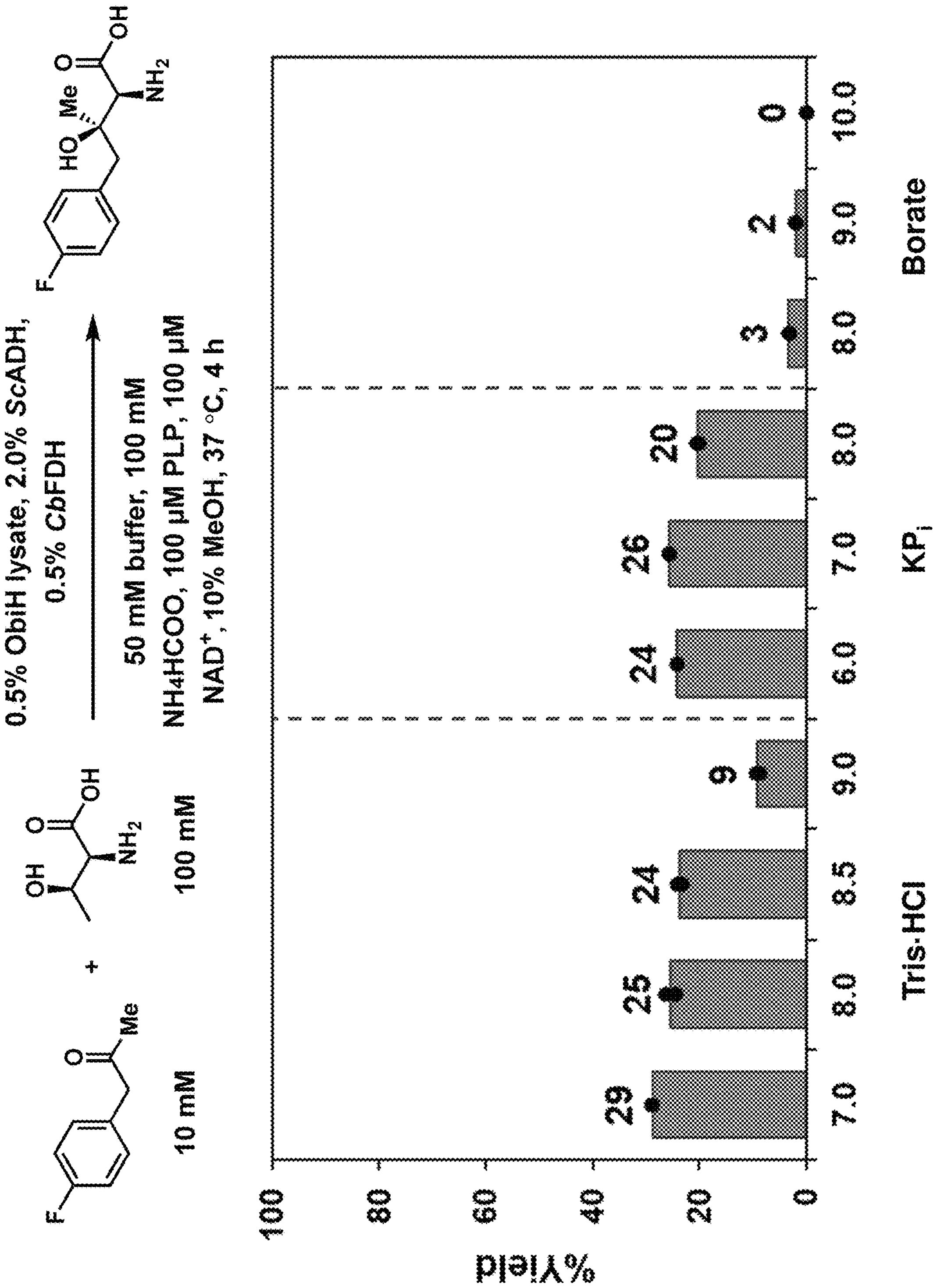
FIG. 9 depicts the results of optimizing the buffer and pH in the ObiH-acetaldehyde reductase cascade. Buffer and pH are shown in the X-axis; present product yield on the Y-axis. The general reaction conditions are shown above the histogram. ("KPi" refers to inorganic potassium phosphate buffer comprising $KH_2PO4$ (monopotassium phosphate) and $K_2HPO_4$ (dipotassium phosphate).)

FIG. 9 is a table showing the effect of buffer composition and pH on an exemplary reaction according to the present method. The reaction is shown at the top of FIG. 9. 100 mM threonine was reacted with 10 mM of 4-fluorobenzyl methyl ketone. The remaining reaction conditions were as noted in FIG. 9 itself. Yields suffered at higher pHs. At pH 8, 9, and 10, using a borate buffer, the highest yields as only 3% (borate, pH 8.0). Using "Tris" (tris(hydroxymethyl)aminomethane) buffer at pH 9.0 only bumped the yield to 9%. Yields ranged from 20% to 29% using Tris or KPi buffers, at pHs ranging from 6.0 to 8.5.

Figure 10:
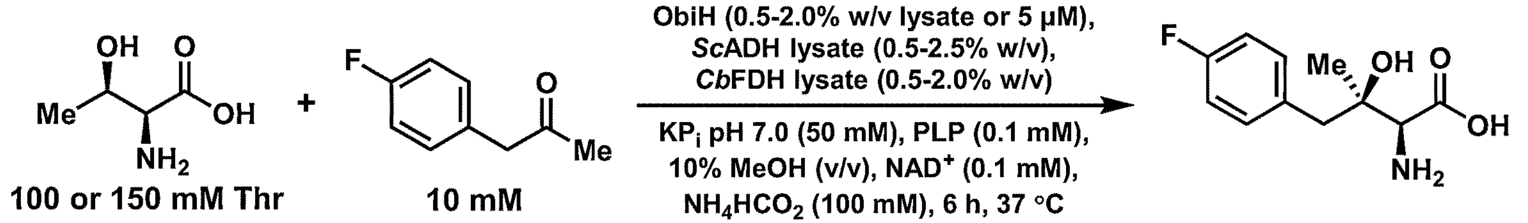
FIG. 10 depicts the results for catalyst ratio optimization of the ObiH-acetaldehyde reductase cascade.

FIG. 10 is a table analogous to FIG. 9, but showing the effect of optimizing enzyme concentration. The reaction and reaction conditions are the same as shown for FIG. 9. The maximum yield, 49% was achieved using the conditions shown in Entry 6: 0.5% w/v ObiH lysate, 2.0% w/v ScADH lysate, 0.5% w/v CbFDH, and 10:1 diasteriomeric ratio ("dr").

Figure 11:
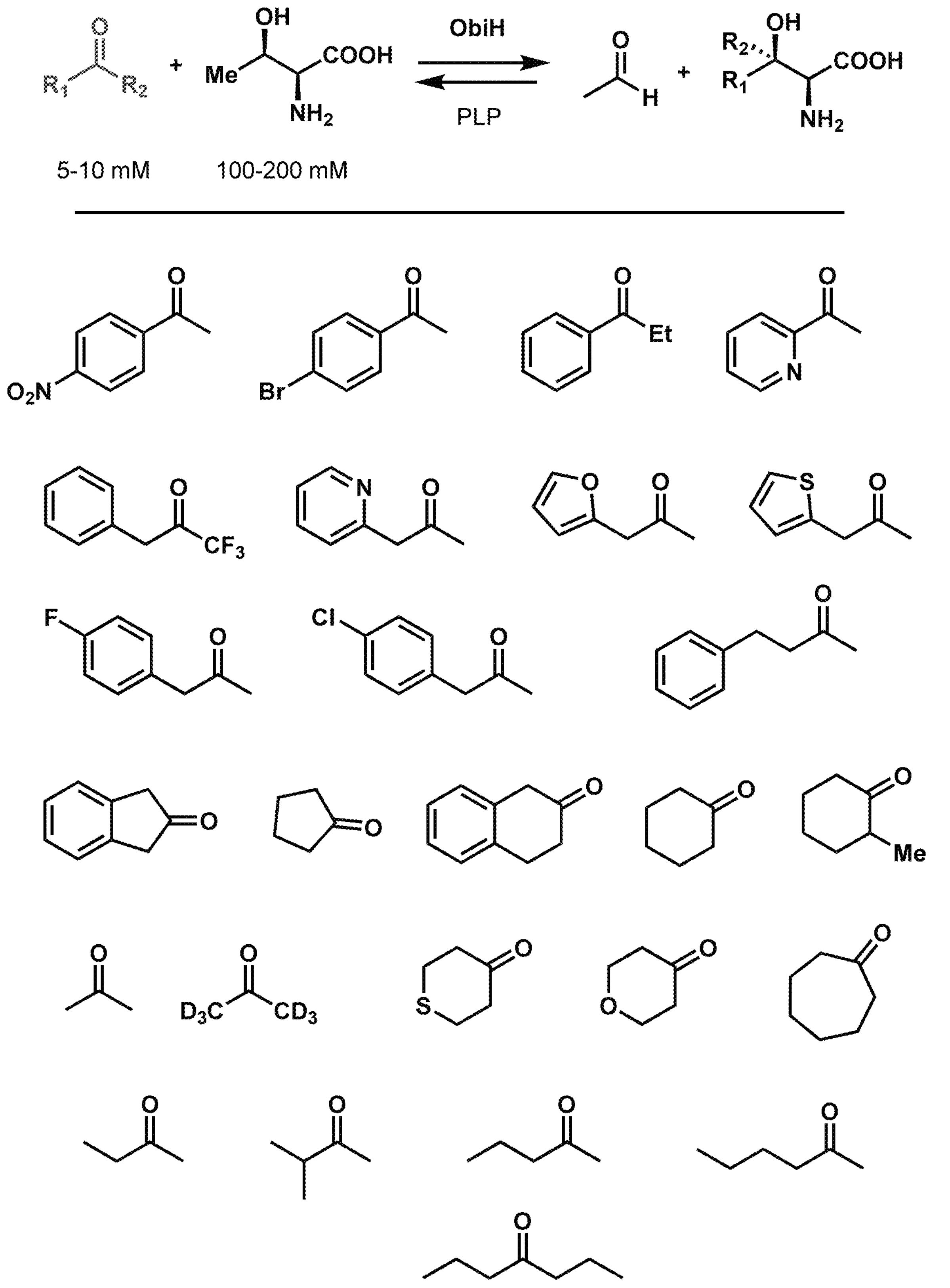
FIG. 11 shows a non-limiting, exemplary group of substrates that have been successfully converted to tertiary β-hydroxy α-amino acids using method disclosed herein. Tertiary β-hydroxy amino acids corresponding to each of the illustrated substrates below have been observed through the ObiH-reductase cascade. The reactions were run using the optimized conditions found in FIG. 9, entry 6 (KPi buffer, pH 7.0).

FIG. 11 presents a selection of the ketone substrates that have been shown to function to yield a tertiary β-hydroxy α-amino acid product using the present method. The ketones include purely aliphatic, symmetric and asymmetric ketones (e.g., methyl ethyl ketone, diethyl ketones), cyclic ketones, heterocyclic ketones, aryl ketones, heteroaryl ketones, etc. For each entry in FIG. 11, tertiary β-hydroxy amino acids corresponding to the ketone substrate have been made and observed using the method disclosed herein. These successful reactions were run using the optimized conditions found in FIG. 9, entry 6.

Figure 12:
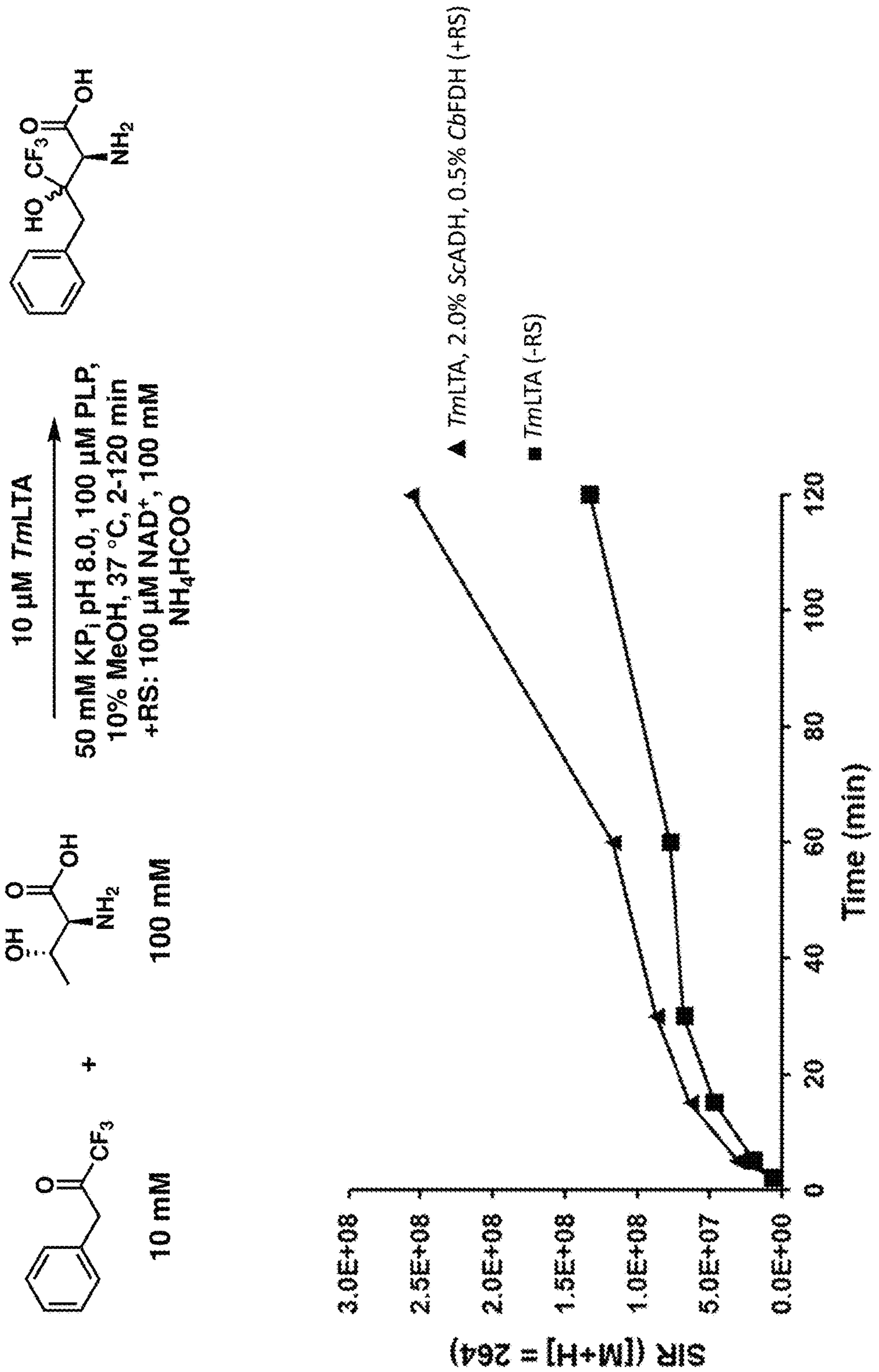
FIG. 12 presents a reaction and a corresponding yield curve showing that TmLTA can catalyze a transaldolase reaction using alloThr as the substrate (a diastereomer of the standard L-Thr). Top trace: 10 μM TmLTA, 2.0% ScADH, 0.5% CbFDH (+RS); bottom trace: 10 μM TmLTA (−RS).

FIG. 12 presents a reaction and a corresponding yield curve showing that TmLTA can catalyze a transaldolase reaction using alloThr as the substrate (a diastereomer of the standard L-Thr). Yields are boosted by using the ScADH and CbFDH cascade. Here, the reaction was as follows:

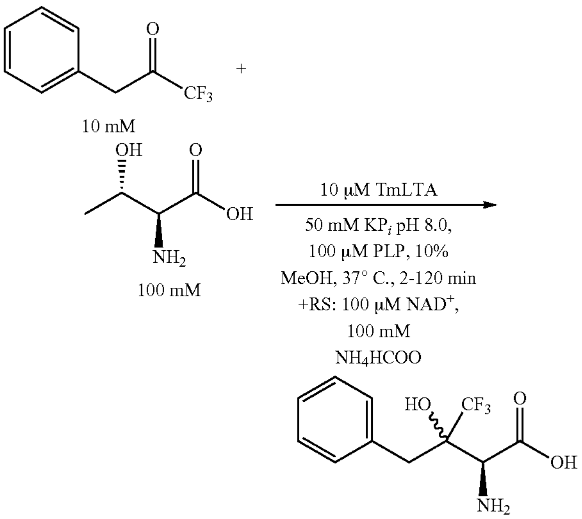

In this particular implementation of the method, any β-hydroxy-amino acid or glycine can be used for the L-TA reaction. Any β-hydroxy-amino acid can be used for the ObiH reaction, but glycine is not preferred.

Substrates that have been tested and shown to yield corresponding product include:

TmLTA

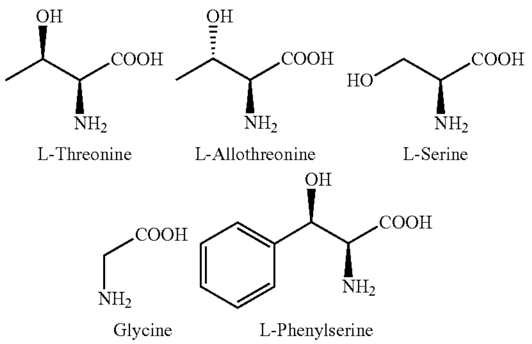

L-Threonine     L-Allothreonine     L-Serine

Glycine     L-Phenylserine

ObiH

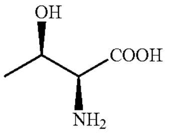

L-Threonine

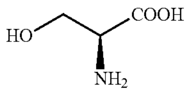

L-Serine

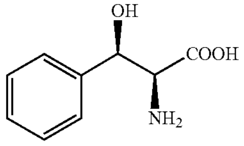

L-Phenylserine

Figure 13:
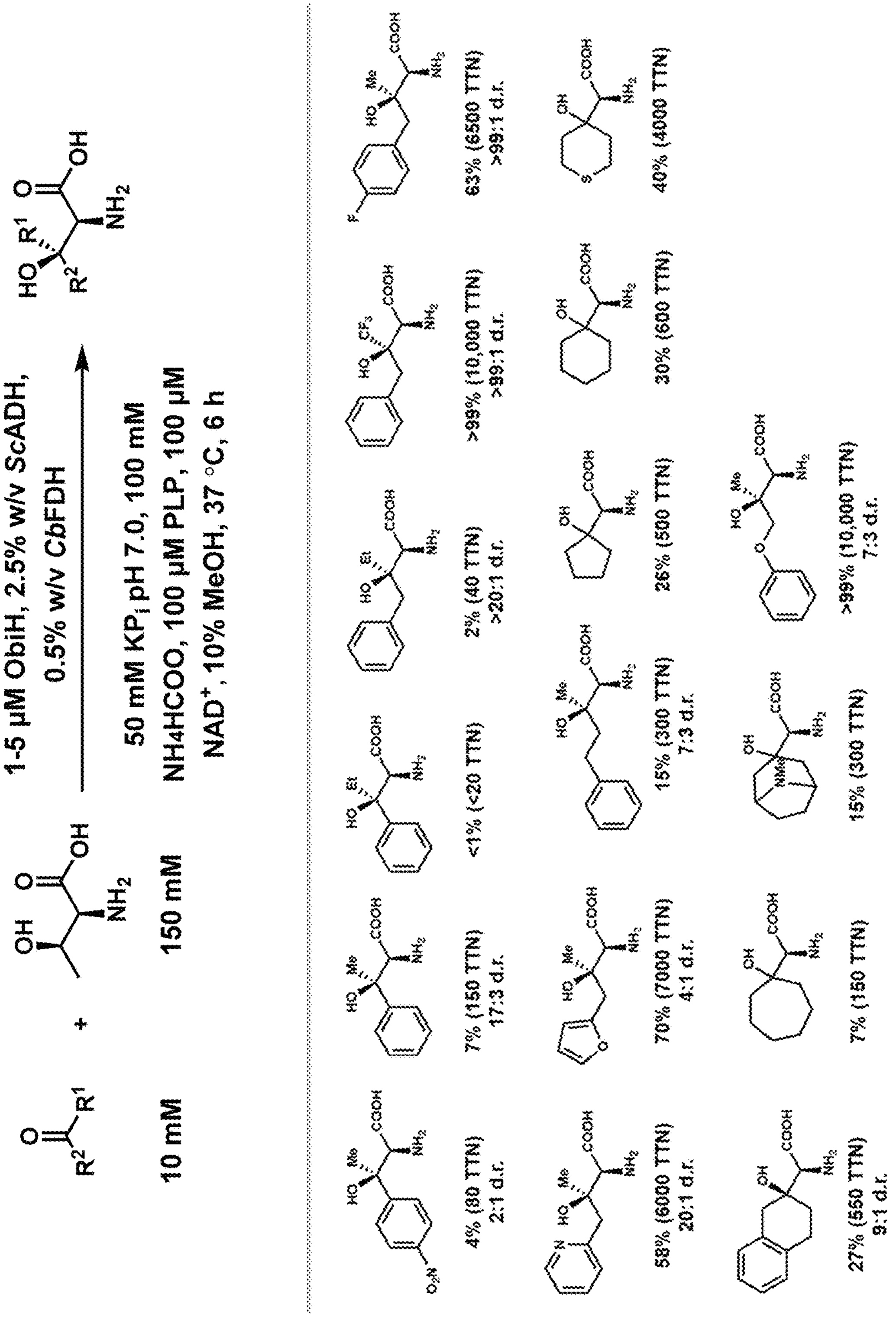
FIG. 13 shows representative analytical scope for ObiH, for compounds made according to the present method, including diastereomeric ratio and total turnover number (TTN).

FIG. 13 shows representative analytical scope for ObiH, for compounds made according to the present method, including diastereomeric ratio and total turnover number (TTN). The test reaction here was:

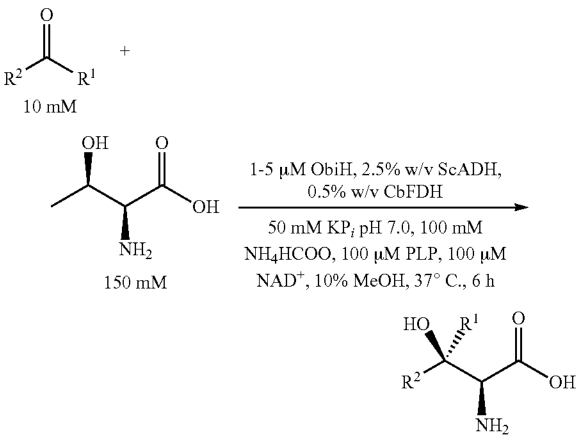

As shown from the wide range of products formed, the reaction is exceedingly flexible and give acceptable yields using a host of different ketone substrates.

Figure 14:
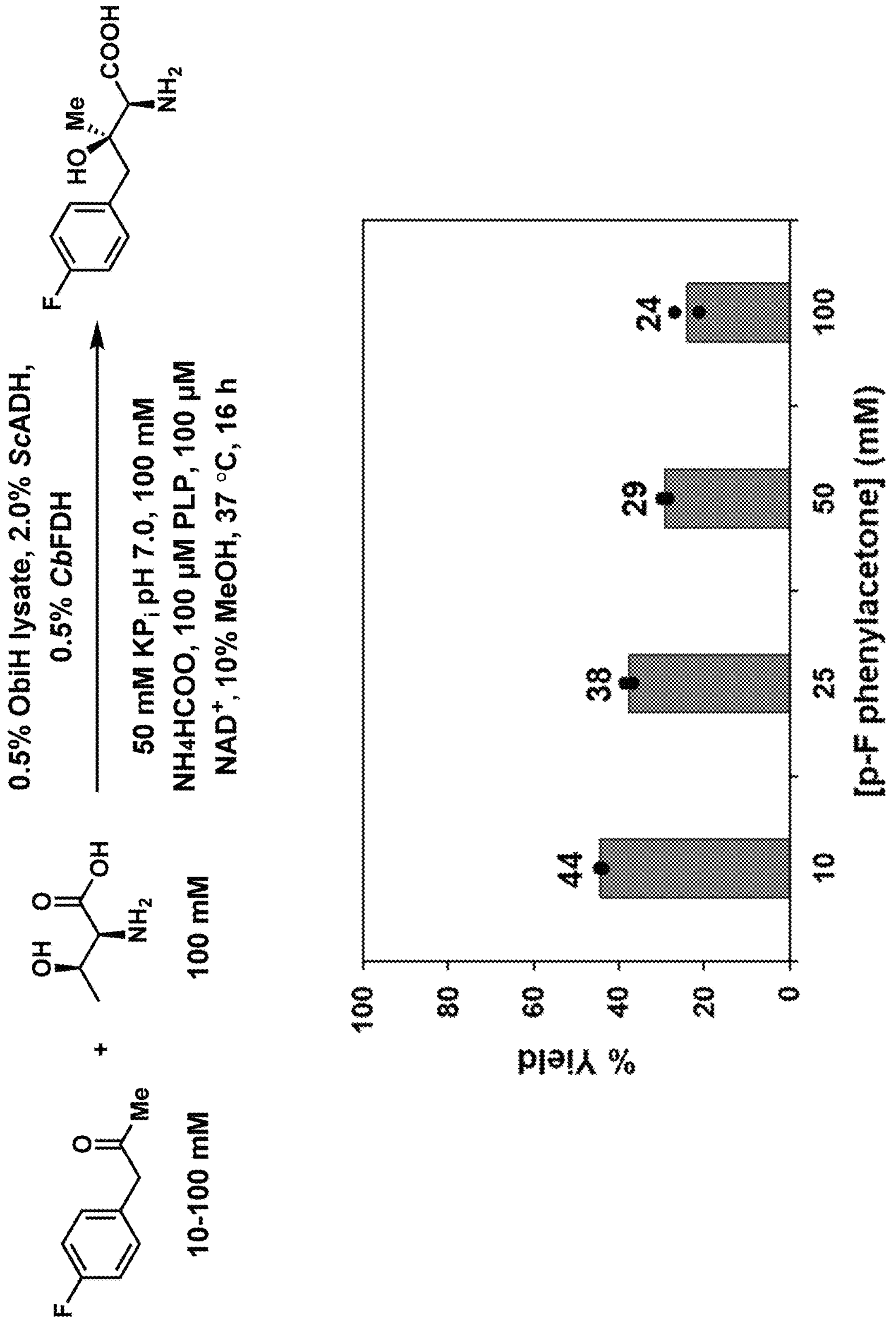
FIG. 14 depicts an exemplary reaction and corresponding yield histogram showing that the method gives good yields at high substrate concentrations.

FIG. 14 depicts the results of an exemplary reaction to investigate the impact of substrate concentration on product yield. The corresponding yield histogram shows that the method gives good yields at high substrate concentrations. The reaction here was:

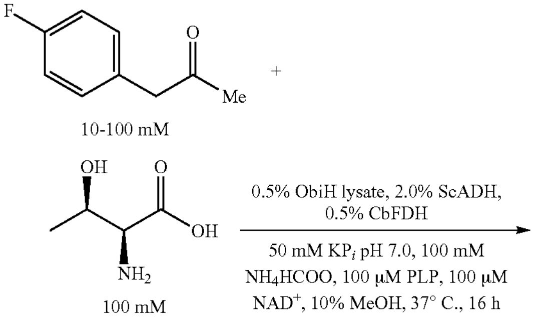

-continued

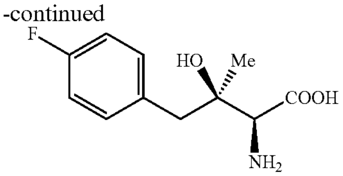

Figure 15:
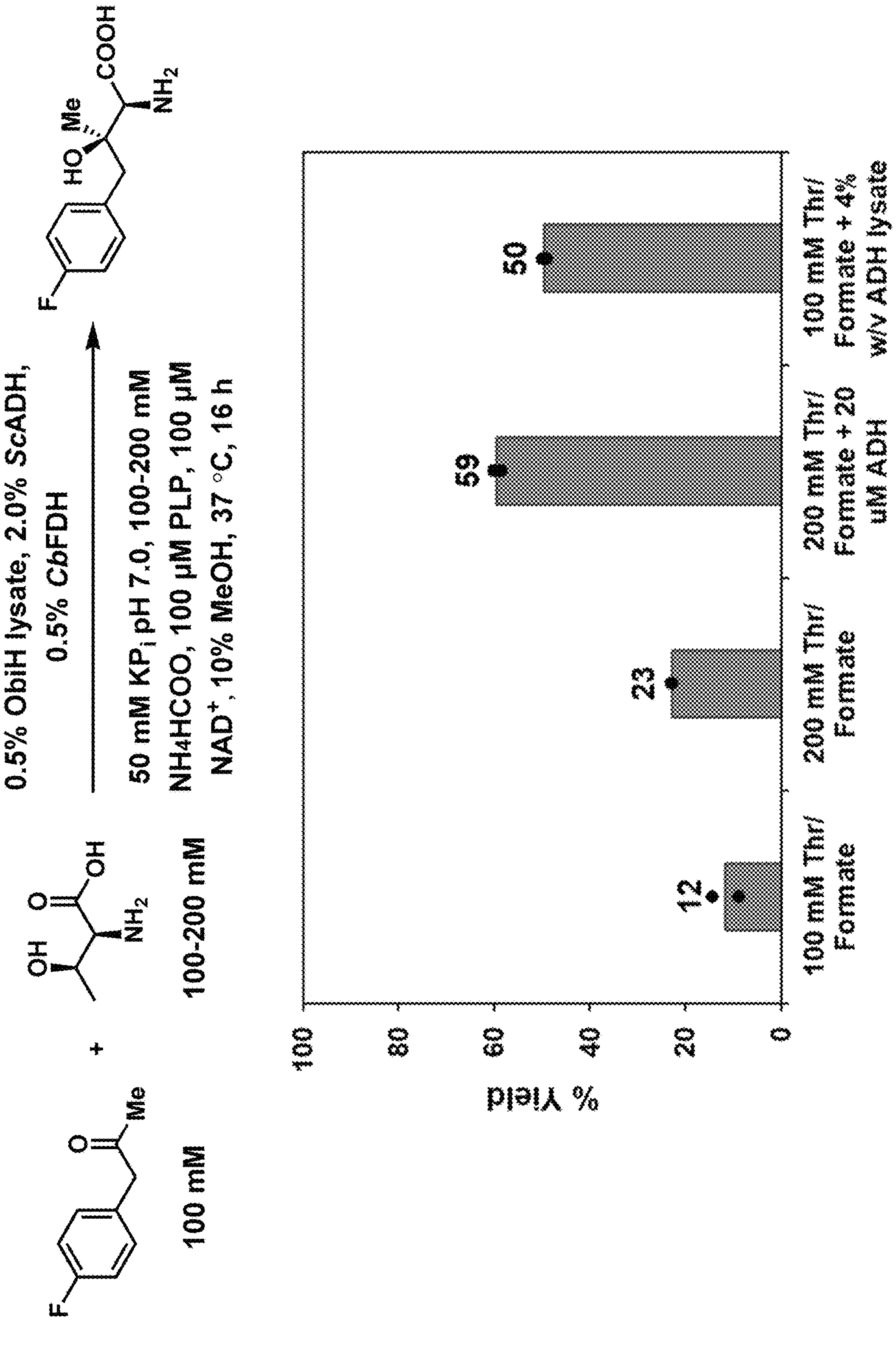
FIG. 15 is an exemplary reaction using 100 mM of ketone substrate and showing that yield was improved by adding more Thr/formate and ADH to the reaction.

FIG. 15 is an exemplary reaction showing that using 100 mM of ketone substrate, yields were improved by adding more Thr and formate to the reaction. Here, the reaction was the same as shown in FIG. 14. As shown in the histogram, the percent yield was very significantly improved by adding additional threonine and/or additional ADH.

Figure 16:
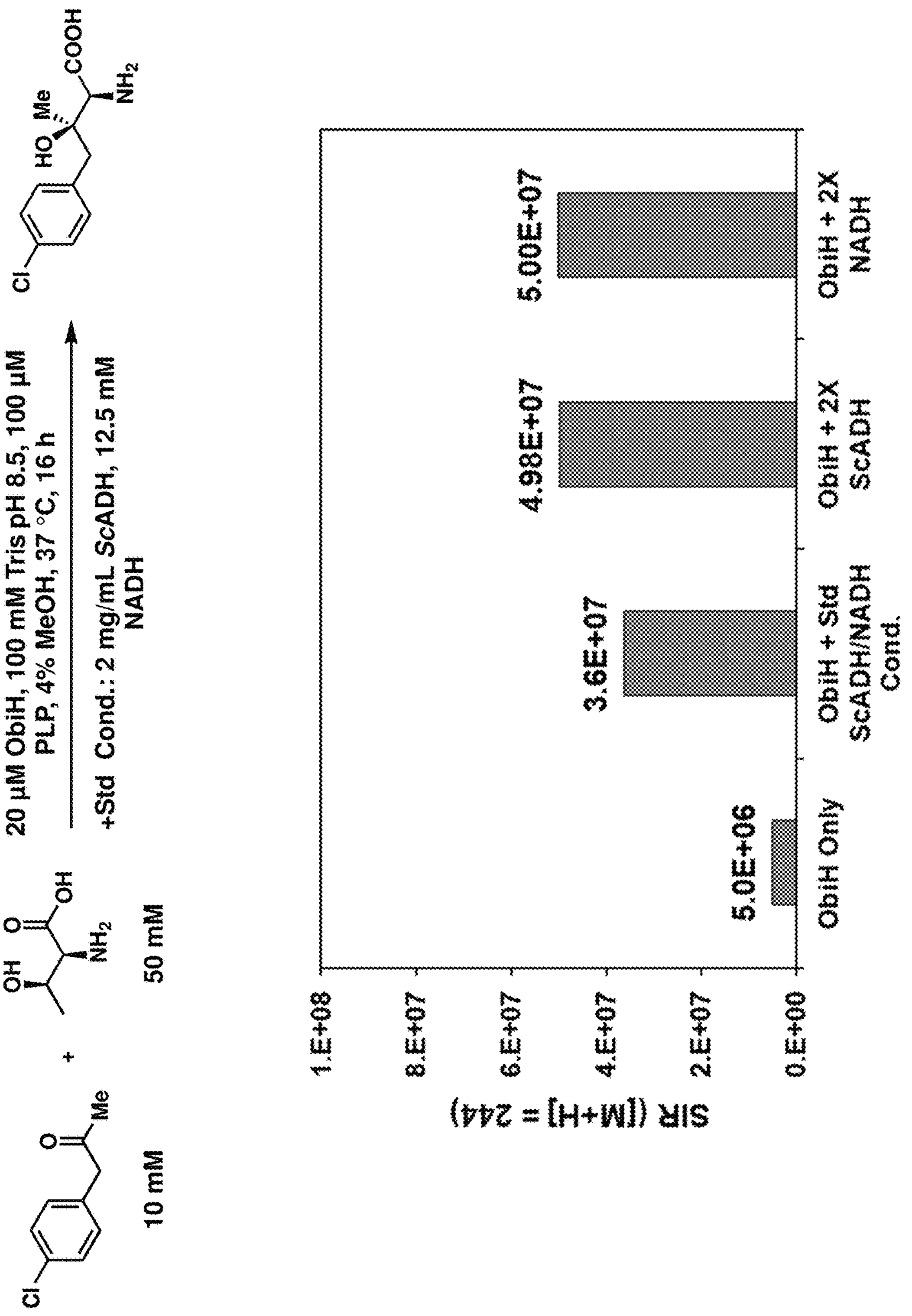
FIG. 16 is an exemplary reaction showing stand-alone ScADH is sufficient for providing increase in activity, which can be improved by adding more ADH and NADH.

FIG. 16 is an exemplary reaction showing stand-alone ScADH is sufficient for providing increase in activity, which can be improved by adding more ADH and NADH. The reaction is as follows:

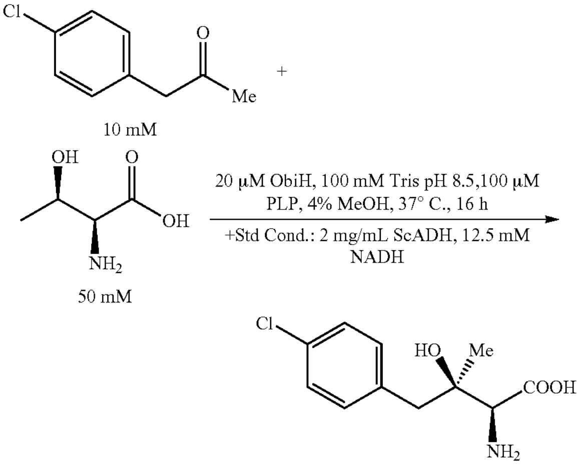

Experimental Procedure

Cloning and Expression of ObiH and ScADH:

A codon-optimized copy of each was inserted into a pET-28b(+) vector (Millipore Sigma, Burlington, Massachusetts, USA) by the Gibson Assembly method. Gibson D G, Young L, Chuang R Y, Venter J C, Hutchison C A 3rd, Smith H O (2009). "Enzymatic assembly of DNA molecules up to several hundred kilobases," *Nature Methods* 6 (5): 343-345. BL21 (DE3) *E. coli* cells (New England Biolabs Inc. Ipswich, Massachusetts, USA) were subsequently transformed with the resulting cyclized DNA product via electroporation. After 45 min of recovery in Luria-Burtani (LB) media at 37° C., cells were plated onto LB plates with 50 μg/mL kanamycin (Kan) and incubated overnight. Single colonies were used to inoculate 5 mL LB+50 μg/mL Kan, which were grown overnight at 37° C., 200 rpm. Expression cultures, typically 1 L of Terrific Broth (TB)+50 μg/mL Kan (TB-Kan), were inoculated from these starter cultures and shaken (200 rpm) at 37° C. After 3 hours ($OD_{600}$=~0.6), the expression cultures were chilled on ice. After 30 min on ice, expression is induced with 0.5 mM IPTG, and the cultures were expressed for 16 hours at 20° C. with shaking at 200 rpm. Cells were then harvested by centrifugation at 4,300×g at 4° C. for 15 min. Cell pellets were frozen and stored at −20° C. until purification.

Cloning and Expression of TmLTA and CbFDH:

A codon-optimized copy of each was inserted into a pET-22b(+) vector (Millipore Sigma, Burlington, Massachusetts, USA) by the Gibson Assembly method. BL21 (DE3) *E. coli* cells were subsequently transformed with the resulting cyclized DNA product via electroporation. After 45 min of recovery in Luria-Burtani (LB) media at 37° C., cells were plated onto LB plates with either 100 μg/mL ampicillin (Amp) and incubated overnight. Single colonies were used to inoculate 5 mL LB+100 μg/mL Amp, which were grown overnight at 37° C., 200 rpm. Expression cultures, typically 1 L of Terrific Broth (TB)+50 μg/mL Amp (TB-Amp), were inoculated from these starter cultures and shaken (200 rpm) at 37° C. After 3 hours ($OD_{600}$=–0.6), the expression cultures were chilled on ice. After 30 min on ice, expression is induced with 0.5 mM IPTG, and the cultures were expressed for 16 hours at 20° C. with shaking at 200 rpm. Cells were then harvested by centrifugation at 4,300×g at 4° C. for 15 min. Cell pellets were frozen and stored at –20° C. until purification.

Purification of ObiH, TmLTA, ScADH and CbFDH:

To purify each protein, cell pellets were thawed on ice and then resuspended in lysis buffer (50 mM potassium phosphate buffer (pH=8.0), 150 mM NaCl, and (for ObiH and TmLTA only) 400 μM pyridoxal 5'-phosphate (PLP). A volume of 4 mL of lysis buffer per gram of wet cell pellet was used. After resuspension, the cell suspension was placed on ice in a metal container and subjected to lysis using a sonication device at 50% power for 5 sec on and 10 sec off for a total time of 5 min. The resulting lysate was then spun down at 50,000×g to pellet cell debris. Ni/NTA beads (Gold Biotechnology, Inc. (doing business as "GoldBio") St. Louis, Missouri, USA) were added to the supernatant and incubated on ice for 45 min prior to purification by Ni-affinity chromatography with a gravity column. The column was washed with 5 column volumes of 20 mM imidazole, 150 mM NaCl, 50 mM potassium phosphate buffer (pH=8.0). Washing with higher concentrations of imidazole resulted in slow protein elution. Each protein was eluted with 250 mM imidazole, 150 mM NaCl, 50 mM potassium phosphate buffer, pH 8.0. For ObiH, elution of the desired protein product was monitored by the disappearance of its bright red color (resulting from the release of ObiH) from the column. FDH and ADH are colorless and their elution was monitored by the addition of 1 μL of eluent to 50 μL of Bradford reagent and evaluating the presence of protein by color change in the reagent (brown to blue). The protein products were dialyzed to <1 μM imidazole in 50 mM potassium phosphate buffer (pH 8.0) with 150 mM NaCl. Purified enzyme was flash frozen in pellet form by pipetting enzyme dropwise into a crystallization dish filled with liquid nitrogen. The enzyme was transferred to a plastic conical and stored at –80° C. until further use. Frozen pellets were thawed at room temperature and centrifuged before use. The concentration of protein was determined by Bradford assay using bovine serum albumin for a standard concentration curve. Generally, this procedure yielded 200-250 mg per L culture for ObiH, 500-600 mg per L culture for TmLTA, 100-120 mg per L culture for FDH and 30-60 mg per L culture for ADH. Protein purity was analyzed by sodium dodecyl sulfate-polyacrylamide (SDS-PAGE) gel electrophoresis using 12% polyacrylamide gels.

Enzymes

L-Threonine Aldolase

L-threonine aldolase (L-TA) includes enzymes falling under Enzyme Commission (EC) number 4.1.2.5. In its native milieu, L-TAs catalyze the cleavage of L-threonine to yield acetaldehyde and glycine. Exemplary L-TA may have an amino acid sequence of SEQ ID NO: 1 or a sequence at least 40%, at least 50%, at least 60%, at least 70%, at least 80%, at least 85%, at least 90%, at least 95%, at least 97%, or at least 99% identical thereto. The coding sequence of SEQ ID NO: 1 is shown as SEQ ID NO: 2.

SEQ ID NO: 1 TmLTA (*Thermotoga maritima*)

(SEQ ID NO: 1)

```
MIDLRSDTVTKPTEEMRKAMAQAEVGDDVYGEDPTINELERLAAETFGKE
AALFVPSGTMGNQVSIMAHTORGDEVILEADSHIFWYEVGAMAVLSGVMP
HPVPGKNGAMDPDDVRKAIRPRNIHFPRTSLIAIENTHNRSGGRVVPLEN
IKEICTIAKEHGINVHIDGARIFNASIASGVPVKEYAGYADSVMFCLSKG
LCAPVGSVVVGDRDFIERARKARKMLGGGMRQAGVLAAAGIIALTKMVDR
LKEDHENARFLALKLKEIGYSVNPEDVKTNMVILRTDNLKVNAHGFIEAL
RNSGVLANAVSDTEIRLVTHKDVSRNDIEEALNIFEKLERKFSLEHHHHH
H
```

SEQ ID NO: 2 TmLTA (*Thermotoga maritima*)

(SEQ ID NO: 2)

```
ATGATCGATCTCAGGTCCGACACCGTTACAAAACCAACAGAAGAGATGAG
AAAAGCCATGGCACAGGCTGAGGTGGGAGACGATGTGTACGGAGAAGATC
CAACCATCAACGAACTCGAAAGGCTCGCCGCAGAGACCTTTGGAAAGGAA
GCGGCTCTCTTTGTACCCTCCGGCACCATGGGAAATCAAGTGAGCATAAT
GGCTCACACCCAGAGGGGCGATGAAGTGATACTGGAGGCAGACAGCCACA
TCTTCTGGTACGAGGTCGGAGCCATGGCGGTTCTCTCCGGAGTCATGCCC
CATCCTGTACCTGGAAAAAATGGAGCCATGGACCCCGATGATGTGAGGAA
GGCCATAAGACCCAGAAACATACACTTCCCCAGAACTTCGCTCATTGCCA
TCGAAAACACACACAACCGTTCCGGTGGAAGAGTGGTCCCGCTTGAAAAC
ATAAAAGAGATTTGCACGATAGCCAAAGAACACGGCATAAACGTTCACAT
AGATGGTGCGAGGATCTTCAACGCCTCAATCGCTTCAGGTGTTCCCGTGA
AGGAGTACGCCGGGTACGCCGATTCCGTGATGTTCTGTCTTTCAAAAGGT
CTCTGCGCACCCGTCGGTTCGGTGGTTGTAGGAGACAGGGACTTCATAGA
AAGAGCGAGAAAGGCGAGAAAGATGCTCGGTGGAGGGATGAGACAGGCAG
GTGTTCTCGCTGCCGCTGGAATAATCGCCTTGACAAAGATGGTAGATCGA
TTGAAAGAAGATCATGAAAACGCCAGATTTCTCGCCCTGAAGTTGAAAGA
AATAGGGTACTCCGTGAATCCCGAAGATGTGAAAACCAACATGGTGATTC
TGAGGACCGACAACCTGAAGGTGAACGCGCACGGGTTCATAGAAGCGCTC
AGAAACAGCGGGGTGCTCGCGAACGCCGTATCCGACACGGAGATCAGACT
GGTAACCCACAAAGACGTTTCAAGAAACGACATAGAAGAGGCTCTGAACA
TCTTCGAAAAACTCTTCAGAAAATTCTCCCTCGAGCACCATCACCATCAC
CATTGA
```

L-Threonine Transaldolase

L-threonine transaldolase (L-T-transA) includes enzymes that in their native milieu catalyze the formation of secondary β-hydroxy α-amino acids. One representative group of L T-transA includes enzymes falling under EC number 2.2.1.4. Exemplary L-T-transA may have an amino acid sequence of SEQ ID NO: 3 or a sequence at least 40%, at least 50%, at least 60%, at least 70%, at least 80%, at least 85%, at least 90%, at least 95%, at least 97%, or at least 99% identical thereto. The coding sequence of SEQ ID NO: 3 is shown as SEQ ID NO: 4.

SEQ ID NO: 3 ObiH (*Pseudomonas fluorescens* ATCC 39502)

(SEQ ID NO: 3)

MGSSHHHHHHSSMSNVKQQTAQIVDWLSSTLGKDHQYREDSLSLTANENY

PSALVRLTSGSTAGAFYHCSFPFEVPAGEWHFPEPGHMNAIADQVRDLGK

TLIGAQAFDWRPNGGSTAEQALMLAACKPGEGFVHFAHRDGGHFALESLA

QKMGIEIFHLPVNPTSLLIDVAKLDEMVRRNPHIRIVILDQSFKLRWQPL

AEIRSVLPDSCTLTYDMSHDGGLIMGGVEDSPLSCGADIVHGNTHKTIPG

PQKGYIGFKSAQHPLLVDTSLWVCPHLQSNCHAEQLPPMWVAFKEMELFG

RDYAAQIVSNAKTLARHLHELGLDVTGESFGFTQTHQVHFAVGDLQKALD

LCVNSLHAGGIRSTNIEIPGKPGVHGIRLGVQAMTRRGMKEKDFEVVARF

IADLYFKKTEPAKVAQQIKEFLQAFPLAPLAYSFDNYLDEELLAAVYQGA

QR

SEQ ID NO: 4 ObiH (*Pseudomonas fluorescens* ATCC 39502)

(SEQ ID NO: 4)

ATGGGCAGCAGCCATCATCATCATCATCACAGCAGCATGTCAAACGTGAA

GCAGCAGACGGCGCAAATCGTAGATTGGTTGTCATCAACCTTGGGGAAAG

ATCACCAATACCGCGAGGACTCCCTTTCACTTACCGCTAACGAGAACTAC

CCGTCGGCATTAGTTCGTTTGACTTCAGGTTCGACCGCCGGCGCATTCTA

CCATTGTTCTTTCCCCTTCGAGGTTCCTGCCGGGGAGTGGCACTTCCCGG

AGCCCGGTCATATGAATGCAATTGCTGACCAGGTTCGTGATTTAGGTAAA

ACCTTGATTGGTGCCCAGGCATTCGACTGGCGTCCAAATGGCGGATCAAC

CGCAGAACAGGCACTTATGCTGGCAGCATGTAAACCGGGAGAGGGGTTCG

TCCATTTTGCTCACCGCGACGGAGGCCATTTCGCTTTAGAATCTCTTGCG

CAAAAGATGGGCATCGAAATTTTCCACTTGCCTGTTAATCCGACCTCTCT

GTTAATCGATGTCGCCAAATTGGATGAAATGGTCCGCCGCAACCCGCATA

TTCGCATTGTCATTCTTGATCAGAGCTTTAAGCTGCGCTGGCAACCCCTG

GCCGAGATTCGTTCAGTTTTACCAGACTCATGCACGTTGACTTATGATAT

GAGTCATGATGGGGGATTAATTATGGGAGGTGTCTTCGATTCCCCCCTTA

GCTGTGGAGCTGACATCGTCCACGGCAATACTCACAAGACGATTCCTGGA

CCGCAAAAGGGGTATATCGGTTTCAAGTCCGCGCAACATCCTTTATTAGT

CGATACAAGTTTATGGGTATGCCCTCACCTTCAAAGTAACTGCCACGCCG

AGCAGCTGCCGCCGATGTGGGTTGCCTTCAAGGAAATGGAATTATTTGGA

CGCGATTACGCTGCCCAAATTGTTTCAAACGCAAAAACCTTGGCTCGCCA

TCTGCATGAACTGGGATTGGACGTGACCGGAGAATCCTTTGGATTCACAC

AGACACATCAGGTCCATTTTGCTGTAGGAGATTTACAGAAAGCGCTTGAT

CTTTGTGTGAATTCATTACATGCTGGAGGTATCCGTTCGACCAATATTGA

AATCCCAGGGAAACCAGGAGTACATGGCATTCGCTTAGGCGTCCAAGCGA

TGACTCGTCGTGGCATGAAGGAGAAAGACTTTGAGGTGGTCGCCCGTTTT

ATCGCCGATCTGTACTTTAAAAAAACGGAACCTGCCAAGGTCGCACAGCA

-continued

AATTAAGGAATTTTTACAGGCGTTTCCGCTTGCACCTTTAGCCTACTCAT

TTGATAACTATCTTGATGAAGAATTATTGGCAGCCGTTTACCAGGGTGCG

CAGCGCTGA

Alcohol Dehydrogenase

Alcohol dehydrogenase (ADH) catalyzes reversible oxidation of alcohol to aldehyde with the simultaneous reduction of NAD(P) to NAD(P)H. ADH includes enzymes falling under EC number 1.1.1.1 and 1.1.1.2. Exemplary ADH may have an amino acid sequence of SEQ ID NO: 5 or a sequence at least 40%, at least 50%, at least 60%, at least 70%, at least 80%, at least 85%, at least 90%, at least 95%, at least 97%, or at least 99% identical thereto. The coding sequence of SEQ ID NO: 5 is shown as SEQ ID NO: 6.

SEQ ID NO: 5 ScADH (*Saccharomyces cerevisiae*)

(SEQ ID NO: 5)

MGSSHHHHHHSSGLVPRGSHMASMTGGQQMGRGSMSIPETQKGVIFYESH

GKLEYKDIPVPKPKANELLINVKYSGVCHTDLHAWHGDWPLPVKLPLVGG

HEGAGVVVGMGENVKGWKIGDYAGIKWLNGSCMACEYCELGNESNCPHAD

LSGYTHDGSFQQYATADAVOAAHIPQGTDLAQVAPILCAGITVYKALKSA

NLMAGHWVAISGAAGGLGSLAVQYAKAMGYRVLGIDGGEGKEELFRSIGG

EVFIDFTKEKDIVGAVLKATDGGAHGVINVSVSEAAIEASTRYVRANGTT

VLVGMPAGAKCCSDVFNQVVKSISIVGSYVGNRADTREALDFFARGLVKS

PIKVVGLSTLPEIYEKMEKGQIVGRYVVDTSK

SEQ ID NO: 6 ScADH (*Saccharomyces cerevisiae*)

(SEQ ID NO: 6)

ATGGGCAGCAGCCATCATCATCATCATCACAGCAGCGGCCTGGTGCCGCG

CGGCAGCCATATGGCTAGCATGACTGGTGGACAGCAAATGGGTCGCGGAT

CCATGAGTATTCCGGAAACACAGAAGGGTGTTATCTTTTATGAGTCACAT

GGCAAATTGGAGTATAAGGATATTCCGGTGCCTAAGCCAAAGGCTAATGA

ACTGCTCATCAATGTTAAATATTCCGGTGTGTGTCACACTGATTTGCATG

CGTGGCATGGCGATTGGCCTCTTCCGGTTAAGCTCCCTCTTGTGGGGGGG

CATGAAGGGGCTGGCGTTGTTGTTGGAATGGGCGAAAATGTAAAAGGTTG

GAAAATCGGAGACTATGCAGGAATAAAATGGCTTAACGGGTCATGTATGG

CCTGCGAATATTGCGAATTGGGCAATGAAAGTAACTGCCCGCACGCTGAC

CTCAGTGGATATACACACGATGGCTCCTTTCAGCAGTATGCCACGGCTGA

TGCCGTGCAAGCGGCACATATTCCTCAGGGGACTGACCTGGCGCAAGTAG

CACCAATTCTTTGTGCAGGCATCACTGTTTATAAAGCTTTGAAGTCAGCT

AATTTGATGGCCGGCCACTGGGTCGCGATTTCAGGAGCCGCTGGCGGGTT

GGGGTCATTAGCCGTGCAATATGCGAAAGCAATGGGCTATCGTGTACTTG

GGATTGATGGAGGCGAAGGCAAAGAGGAATTATTCCGGAGCATTGGCGGT

GAAGTTTTTATTGACTTTACGAAAGAAAAAGATATCGTGGGGGCAGTTCT

GAAAGCAACCGACGGTGGCGCTCATGGCGTGATTAACGTATCCGTGAGTG

AAGCCGCCATCGAAGCATCTACACGTTACGTACGTGCCAATGGTACAACT

GTACTTGTTGGGATGCCCGCCGGCGCCAAGTGTTGCAGTGACGTTTTTAA

TCAGGTTGTGAAGAGTATTAGCATTGTTGGTAGCTATGTGGGTAACCGTG

-continued

CCGACACGCGCGAGGCACTGGACTTCTTTGCACGCGGACTGGTAAAAAGC

CCAATCAAGGTAGTCGGTCTGAGTACGCTGCCAGAGATCTACGAAAAAAT

GGAGAAAGGTCAGATTGTTGGTCGGTATGTTGTCGATACATCAAAATAA

Formate Dehydrogenase

Formate dehydrogenase (FDH) catalyzes reversible oxidation of formate to carbon dioxide with the simultaneous reduction of NAD(P) to NAD(P)H. FDH includes enzymes falling under EC number 1.17.1.9 and 1.17.1.10. Exemplary FDH may have an amino acid sequence of SEQ ID NO: 7 or a sequence at least 40%, at least 50%, at least 60%, at least 70%, at least 80%, at least 85%, at least 90%, at least 95%, at least 97%, or at least 99% identical thereto. The coding sequence of SEQ ID NO: 7 is shown as SEQ ID NO: 8.

SEQ ID NO: 7 CbFDH (*Candida boidinii*)
(SEQ ID NO: 7)

MKIVLVLYDAGKHAADEEKLYGCTENKLGIANWLKDOGHELITTSDKEGE

TSELDKHIPDADIIITTPFHPAYITKERLDKAKNLKLVVVAGVGSDHIDL

DYINQTGKKISVLEVTGSNVVSVAEHVVMTMLVLVRNFVPAHEQIINHDW

EVAAIAKDAYDIEGKTIATIGAGRIGYRVLERLLPFNPKELLYYDYQALP

KEAEEKVGARRVENIEELVAQADIVTVNAPLHAGTKGLINKELLSKFKKG

AWLVNTARGAICVAEDVAAALESGOLRGYGGDVWFPQPAPKDHPWRDMRN

KYGAGNAMTPHYSGTTLDAQTRYAEGTKNILESFFTGKFDYRPQDIILLN

GEYVTKAYGKHDKKLEHHHHHH

SEQ ID NO: 8 CbFDH (*Candida boidinii*)
(SEQ ID NO: 8)

ATGAAGATCGTGTTAGTTTTGTACGATGCCGGAAAACACGCGGCAGATGA

GGAGAAGTTGTACGGATGTACCGAAAATAAGTTGGGTATCGCGAATTGGT

TAAAGGACCAAGGTCATGAGCTGATCACAACATCAGATAAAGAAGGTGAG

ACTTCGGAGCTGGATAAGCATATTCCAGATGCCGACATTATTATTACAAC

ACCTTTTCACCCTGCGTACATCACGAAAGAGCGCCTTGATAAGGCTAAAA

ATCTGAAGCTTGTGGTGGTGGCTGGAGTCGGATCGGATCACATTGACTTA

-continued

GATTACATCAATCAAACGGGAAAGAAGATTTCCGTGTTGGAAGTAACGGG

AAGTAACGTCGTGTCCGTTGCGGAGCACGTCGTGATGACAATGTTAGTTT

TAGTGCGTAACTTCGTGCCCGCGCACGAACAAATTATCAACCATGACTGG

GAGGTGGCCGCTATTGCCAAGGACGCATACGACATTGAAGGGAAGACTAT

CGCGACGATTGGTGCTGGTCGCATCGGTTACCGTGTCCTGGAGCGCTTAT

TGCCGTTTAATCCAAAAGAGCTGTTATACTATGATTACCAAGCACTGCCA

AAAGAGGCTGAGGAGAAAGTCGGCGCCCGTCGTGTAGAGAATATTGAAGA

ATTGGTCGCCCAAGCTGACATCGTAACAGTAAACGCGCCATTGCACGCCG

GCACAAAGGGTTTGATTAACAAGGAGTTACTGAGCAAATTCAAAAAAGGA

GCTTGGCTTGTAAACACTGCTCGCGGCGCAATTTGCGTAGCAGAAGACGT

CGCTGCTGCCCTGGAGTCAGGACAGTTGCGCGGGTATGGAGGTGACGTAT

GGTTCCCACAGCCAGCTCCTAAGGATCACCCTTGGCGCGATATGCGTAAC

AAGTACGGTGCTGGAAACGCAATGACGCCTCATTATTCCGGTACGACGTT

GGATGCACAAACTCGTTATGCAGAGGGCACAAAAAATATTTTGGAATCCT

TTTTCACAGGCAAGTTCGACTATCGTCCTCAAGATATCATTCTGCTTAAT

GGGGAGTATGTGACAAAGGCATACGGTAAGCATGATAAGAAACTCGAGCA

CCATCACCATCACCATTGA

Other enzymes may also be used to catalyze the reversible reduction of NAD(P) to NAD(P)H, including glucose dehydrogenases ("GDH's", E.C. 1.1.1.47; CAS No. CAS No. 9028-53-9) such as the glucose dehydrogenase from *Bacillus megaterium* ("BmGDH"). See Xiu et al. (2022) "Multi-enzyme cascade for sustainable synthesis of L-threo-phenylserine by modulating aldehydes inhibition and kinetic/thermodynamic controls," *Systems Microbiology and Biomanufacturing* 2:705-715. GDH's in general and BmGDH in particular are commercially available from several national and international sources. For example, BmGDH is commercially available from Sigma-Aldrich (St. Louis, Missouri, USA) as a lyophilized powder, catalog no. G7653. Likewise, glucose dehydrogenase from *Pseudomonas* sp. is also commercially available from Sigma-Aldrich, catalog no. 19359.

What is claimed is:

1. A method to make an amino acid having a tertiary alcohol sidechain, the method comprising reacting a pyridoxal-phosphate (PLP)-dependent enzyme selected from the group consisting of an L-threonine aldolase, an L-threonine transaldolase, and a combination thereof, with a ketone substrate and a primary or secondary β-hydroxy α-amino acid for a time, at a temperature, and at a pH wherein the reaction yields a tertiary β-hydroxy α-amino acid.

2. The method of claim 1, wherein the PLP-dependent enzyme is an L-threonine aldolase.

3. The method of claim 2, wherein the L-threonine aldolase has an amino acid sequence at least 80% identical to SEQ. ID. NO: 1.

4. The method of claim 2, wherein the L-threonine aldolase has an amino acid sequence at least 90% identical to SEQ. ID. NO: 1.

5. The method of claim 2, wherein the L-threonine aldolase has an amino acid sequence at least 95% identical to SEQ. ID. NO: 1.

6. The method of claim 3, wherein the PLP-dependent enzyme is ObiH.

7. The method of claim 1, wherein the time is from about 1 hour to about 12 hours, the temperature is from about 30° C. to about 50° C., and the pH is from about 6 to about 8.

8. The method of claim 1, further comprising reacting the PLP-dependent enzyme and the ketone substrate in the presence of a reducing system.

9. The method of claim 1, wherein the ketone substrate further comprises an electron-withdrawing group.

10. The method of claim 9, wherein the electron-withdrawing group is selected from the group consisting of halo, haloalkyl, $—NH_3^+$, $—NO_2$, $—CH{=}CH_2$, —CN, $—SO_3H$, —C(=O)OH, —C(=O)H, —C(=O)R, —C(=O)OR, and $—NR_3^+$, where R is alkyl.

11. The method of claim 1, wherein the primary or secondary β-hydroxy α-amino acid is selected from the group consisting of serine, threonine, and 3-phenyl serine.

12. The method of claim 1, further comprising reducing aldehyde by-products formed in the reaction.

13. The method of claim 12, comprising reducing the aldehyde by-products by contacting them with an alcohol dehydrogenase in the presence of NAD(P)H, wherein the alcohol dehydrogenase reduces at least a portion of the aldehyde by-products, and NAD(P)+ is generated.

14. The method of claim 13, wherein the alcohol dehydrogenase has an amino acid sequence at least 80% identical to SEQ. ID. NO: 5.

15. The method of claim 13, wherein the alcohol dehydrogenase has an amino acid sequence at least 90% identical to SEQ. ID. NO: 5.

16. The method of claim 13, wherein the alcohol dehydrogenase has an amino acid sequence at least 95% identical to SEQ. ID. NO: 5.

17. The method of claim 13, further comprising regenerating NAD(P)H from the NAD(P)+ by contacting the NAD (P)+ with a formate dehydrogenase or a glucose dehydrogenase.

18. The method of claim 17, wherein the formate dehydrogenase has an amino acid sequence at least 80% identical to SEQ. ID. NO: 7.

19. The method of claim 17, wherein the formate dehydrogenase has an amino acid sequence at least 90% identical to SEQ. ID. NO: 7.

20. The method of claim 17, wherein the formate dehydrogenase has an amino acid sequence at least 95% identical to SEQ. ID. NO: 7.

21. The method of claim 13, wherein the NAD(P)+ is contacted with a glucose dehydrogenase.

22. The method of claim 21, wherein the glucose dehydrogenase is derived from *Bacillus megaterium* or *Pseudomonas* sp.

23. The method of claim 1, wherein the PLP-dependent enzyme is an L-threonine transaldolase.

24. The method of claim 23, wherein the L-threonine transaldolase has an amino acid sequence at least 80% identical to SEQ. ID. NO: 3.

25. The method of claim 23, wherein the L-threonine transaldolase has an amino acid sequence at least 90% identical to SEQ. ID. NO: 3.

26. The method of claim 23, wherein the L-threonine transaldolase has an amino acid sequence at least 95% identical to SEQ. ID. NO: 3.

* * * * *

SEQUENCE LISTING

```
Sequence total quantity: 8
SEQ ID NO: 1            moltype = AA  length = 351
FEATURE                 Location/Qualifiers
source                  1..351
                        mol_type = protein
                        organism = Thermotoga maritima
SEQUENCE: 1
MIDLRSDTVT KPTEEMRKAM AQAEVGDDVY GEDPTINELE RLAAETFGKE AALFVPSGTM  60
GNQVSIMAHT QRGDEVILEA DSHIFWYEVG AMAVLSGVMP HPVPGKNGAM DPDDVRKAIR  120
PRNIHFPRTS LIAIENTHNR SGGRVVPLEN IKEICTIAKE HGINVHIDGA RIFNASIASG  180
VPVKEYAGYA DSVMFCLSKG LCAPVGSVVV GDRDFIERAR KARKMLGGGM RQAGVLAAAG  240
IIALTKMVDR LKEDHENARF LALKLKEIGY SVNPEDVKTN MVILRTDNLK VNAHGFIEAL  300
RNSGVLANAV SDTEIRLVTH KDVSRNDIEE ALNIFEKLFR KFSLEHHHHH H           351

SEQ ID NO: 2            moltype = DNA  length = 1056
FEATURE                 Location/Qualifiers
source                  1..1056
                        mol_type = genomic DNA
                        organism = Thermotoga maritima
SEQUENCE: 2
atgatcgatc tcaggtccga caccgttaca aaaccaacag aagagatgag aaaagccatg  60
gcacaggctg aggtgggaga cgatgtgtac ggagaagatc caaccatcaa cgaactcgaa  120
```

-continued

```
aggctcgccg cagagacctt tggaaaggaa gcggctctct ttgtaccctc cggcaccatg  180
ggaaatcaag tgagcataat ggctcacacc cagaggggcg atgaagtgat actggaggca  240
gacagccaca tcttctggta cgaggtcgga gccatggcgg ttctctccgg agtcatgccc  300
catcctgtac ctggaaaaaa tggagccatg gaccccgatg atgtgaggaa ggccataaga  360
cccagaaaca tacacttccc cagaacttcg ctcattgcca tcgaaaacac acacaaccgt  420
tccggtggaa gagtggtccc gcttgaaaac ataaaagaga tttgcacgat agccaaagaa  480
cacggcataa acgttcacat agatggtgcg aggatcttca acgcctcaat cgcttcaggt  540
gttcccgtga aggagtacgc cgggtacgcc gattccgtga tgttctgtct ttcaaaaggt  600
ctctgcgcac ccgtcggttc ggtggttgta ggagacaggg acttcataga aagagcgaga  660
aaggcgagaa agatgctcgg tggagggatg agacaggcag gtgttctcgc tgccgctgga  720
ataatcgcct tgacaaagat ggtagatcga ttgaaagaag atcatgaaaa cgccagattt  780
ctcgccctga agttgaaaga aatagggtac tccgtgaatc ccgaagatgt gaaaaccaac  840
atggtgattc tgaggaccga caacctgaag gtgaacgcgc acgggttcat agaagcgctc  900
agaaacagcg gggtgctcgc gaacgccgta tccgacacgg agatcagact ggtaacccac  960
aaagacgttt caagaaacga catagaagag gctctgaaca tcttcgaaaa actcttcaga  1020
aaattctccc tcgagcacca tcaccatcac cattga                            1056

SEQ ID NO: 3            moltype = AA  length = 452
FEATURE                 Location/Qualifiers
source                  1..452
                        mol_type = protein
                        organism = Pseudomonas fluorescens
SEQUENCE: 3
MGSSHHHHHH SSMSNVKQQT AQIVDWLSST LGKDHQYRED SLSLTANENY PSALVRLTSG  60
STAGAFYHCS FPFEVPAGEW HFPEPGHMNA IADQVRDLGK TLIGAQAFDW RPNGGSTAEQ  120
ALMLAACKPG EGFVHFAHRD GGHFALESLA QKMGIEIFHL PVNPTSLLID VAKLDEMVRR  180
NPHIRIVILD QSFKLRWQPL AEIRSVLPDS CTLTYDMSHD GGLIMGGVFD SPLSCGADIV  240
HGNTHKTIPG PQKGYIGFKS AQHPLLVDTS LWVCPHLQSN CHAEQLPPMW VAFKEMELFG  300
RDYAAQIVSN AKTLARHLHE LGLDVTGESF GFTQTHQVHF AVGDLQKALD LCVNSLHAGG  360
IRSTNIEIPG KPGVHGIRLG VQAMTRRGMK EKDFEVVARF IADLYFKKTE PAKVAQQIKE  420
FLQAFPLAPL AYSFDNYLDE ELLAAVYQGA QR                                452

SEQ ID NO: 4            moltype = DNA  length = 1359
FEATURE                 Location/Qualifiers
source                  1..1359
                        mol_type = genomic DNA
                        organism = Pseudomonas fluorescens
SEQUENCE: 4
atgggcagca gccatcatca tcatcatcac agcagcatgt caaacgtgaa gcagcagacg  60
gcgcaaatcg tagattggtt gtcatcaacc ttggggaaag atcaccaata ccgcgaggac  120
tccctttcac ttaccgctaa cgagaactac ccgtcggcat tagttcgttt gacttcaggt  180
tcgaccgccg gcgcattcta ccattgttct ttccccttcg aggttcctgc cggggagtgg  240
cacttcccgg agcccggtca tatgaatgca attgctgacc aggttcgtga tttaggtaaa  300
accttgattg gtgcccaggc attcgactgg cgtccaaatg gcggatcaac cgcagaacag  360
gcacttatgc tggcagcatg taaaccggga gaggggttcg tccattttgc tcaccgcgac  420
ggaggccatt tcgctttaga atctcttgcg caaaagatgg gcatcgaaat tttccacttg  480
cctgttaatc cgacctctct gttaatcgat gtcgccaaat tggatgaaat ggtccgccgc  540
aacccgcata ttcgcattgt cattcttgat cagagcttta agctgcgctg gcaacccctg  600
gccgagattc gttcagtttt accagactca tgcacgttga cttatgatat gagtcatgat  660
gggggattaa ttatgggagg tgtcttcgat tcccccctta gctgtggagc tgacatcgtc  720
cacggcaata ctcacaagac gattcctgga ccgcaaaagg ggtatatcgg tttcaagtcc  780
gcgcaacatc ctttattagt cgatacaagt ttatgggtat gccctcacct tcaaagtaac  840
tgccacgccg agcagctgcc gccgatgtgg gttgccttca aggaaatgga attatttgga  900
cgcgattacg ctgcccaaat tgtttcaaac gcaaaaacct tggctcgcca tctgcatgaa  960
ctgggattgg acgtgaccgg agaatccttt ggattcacac agacacatca ggtccatttt  1020
gctgtaggag atttacagaa agcgcttgat ctttgtgtga attcattaca tgctggaggt  1080
atccgttcga ccaatattga aatcccaggg aaaccaggag tacatggcat tcgcttaggc  1140
gtccaagcga tgactcgtcg tggcatgaag gagaaagact ttgaggtggt cgcccgtttt  1200
atcgccgatc tgtactttaa aaaaacggaa cctgccaagg tcgcacagca aattaaggaa  1260
tttttacagg cgtttccgct tgcaccttta gcctactcat ttgataacta tcttgatgaa  1320
gaattattgg cagccgttta ccagggtgcg cagcgctga                         1359

SEQ ID NO: 5            moltype = AA  length = 382
FEATURE                 Location/Qualifiers
source                  1..382
                        mol_type = protein
                        organism = Saccharomyces cerevisiae
SEQUENCE: 5
MGSSHHHHHH SSGLVPRGSH MASMTGGQQM GRGSMSIPET QKGVIFYESH GKLEYKDIPV  60
PKPKANELLI NVKYSGVCHT DLHAWHGDWP LPVKLPLVGG HEGAGVVVGM GENVKGWKIG  120
DYAGIKWLNG SCMACEYCEL GNESNCPHAD LSGYTHDGSF QQYATADAVQ AAHIPQGTDL  180
AQVAPILCAG ITVYKALKSA NLMAGHWVAI SGAAGGLGSL AVQYAKAMGY RVLGIDGGEG  240
KEELFRSIGG EVFIDFTKEK DIVGAVLKAT DGGAHGVINV SVSEAAIEAS TRYVRANGTT  300
VLVGMPAGAK CCSDVFNQVV KSISIVGSYV GNRADTREAL DFFARGLVKS PIKVVGLSTL  360
PEIYEKMEKG QIVGRYVVDT SK                                           382

SEQ ID NO: 6            moltype = DNA  length = 1149
FEATURE                 Location/Qualifiers
source                  1..1149
```

-continued

```
                        mol_type = genomic DNA
                        organism = Saccharomyces cerevisiae
SEQUENCE: 6
atgggcagca gccatcatca tcatcatcac agcagcggcc tggtgccgcg cggcagccat  60
atggctagca tgactggtgg acagcaaatg ggtcgcggat ccatgagtat tccggaaaca  120
cagaagggtg ttatctttta tgagtcacat ggcaaattgg agtataagga tattccggtg  180
cctaagccaa aggctaatga actgctcatc aatgttaaat attccggtgt gtgtcacact  240
gatttgcatg cgtggcatgg cgattggcct cttccggtta agctccctct tgtggggggg  300
catgaagggg ctggcgttgt tgttggaatg ggcgaaaatg taaaaggttg gaaaatcgga  360
gactatgcag gaataaaatg gcttaacggg tcatgtatgg cctgcgaata ttgcgaattg  420
ggcaatgaaa gtaactgccc gcacgctgac ctcagtggat atacacacga tggctccttt  480
cagcagtatg ccacggctga tgccgtgcaa gcggcacata ttcctcaggg gactgacctg  540
gcgcaagtag caccaattct ttgtgcaggc atcactgttt ataaagcttt gaagtcagct  600
aatttgatgg ccggccactg ggtcgcgatt tcaggagccg ctggcgggtt ggggtcatta  660
gccgtgcaat atgcgaaagc aatgggctat cgtgtacttg ggattgatgg aggcgaaggc  720
aaagaggaat tattccggag cattggcggt gaagttttta ttgactttac gaaagaaaaa  780
gatatcgtgg gggcagttct gaaagcaacc gacggtggcg ctcatggcgt gattaacgta  840
tccgtgagtg aagccgccat cgaagcatct acacgttacg tacgtgccaa tggtacaact  900
gtacttgttg ggatgcccgc cggcgccaag tgttgcagtg acgtttttaa tcaggttgtg  960
aagagtatta gcattgttgg tagctatgtg ggtaaccgtg ccgacacgcg cgaggcactg  1020
gacttctttg cacgcggact ggtaaaaagc ccaatcaagg tagtcggtct gagtacgctg  1080
ccagagatct acgaaaaaat ggagaaaggt cagattgttg gtcggtatgt tgtcgataca  1140
tcaaaataa                                                          1149

SEQ ID NO: 7            moltype = AA  length = 372
FEATURE                 Location/Qualifiers
source                  1..372
                        mol_type = protein
                        organism = Candida boidinii
SEQUENCE: 7
MKIVLVLYDA GKHAADEEKL YGCTENKLGI ANWLKDQGHE LITTSDKEGE TSELDKHIPD  60
ADIIITTPFH PAYITKERLD KAKNLKLVVV AGVGSDHIDL DYINQTGKKI SVLEVTGSNV  120
VSVAEHVVMT MLVLVRNFVP AHEQIINHDW EVAAIAKDAY DIEGKTIATI GAGRIGYRVL  180
ERLLPFNPKE LLYYDYQALP KEAEEKVGAR RVENIEELVA QADIVTVNAP LHAGTKGLIN  240
KELLSKFKKG AWLVNTARGA ICVAEDVAAA LESGQLRGYG GDVWFPQPAP KDHPWRDMRN  300
KYGAGNAMTP HYSGTTLDAQ TRYAEGTKNI LESFFTGKFD YRPQDIILLN GEYVTKAYGK  360
HDKKLEHHHH HH                                                      372

SEQ ID NO: 8            moltype = DNA  length = 1119
FEATURE                 Location/Qualifiers
source                  1..1119
                        mol_type = genomic DNA
                        organism = Candida boidinii
SEQUENCE: 8
atgaagatcg tgttagtttt gtacgatgcc ggaaaacacg cggcagatga ggagaagttg  60
tacggatgta ccgaaaataa gttgggtatc gcgaattggt taaaggacca aggtcatgag  120
ctgatcacaa catcagataa agaaggtgag acttcggagc tggataagca tattccagat  180
gccgacatta ttattacaac accttttcac cctgcgtaca tcacgaaaga gcgccttgat  240
aaggctaaaa atctgaagct tgtggtggtg gctggagtcg gatcggatca cattgactta  300
gattacatca atcaaacggg aaagaagatt tccgtgttgg aagtaacggg aagtaacgtc  360
gtgtccgttg cggagcacgt cgtgatgaca atgttagttt tagtgcgtaa cttcgtgccc  420
gcgcacgaac aaattatcaa ccatgactgg gaggtggccg ctattgccaa ggacgcatac  480
gacattgaag ggaagactat cgcgacgatt ggtgctggtc gcatcggtta ccgtgtcctg  540
gagcgcttat tgccgtttaa tccaaaagag ctgttatact atgattacca agcactgcca  600
aaagaggctg aggagaaagt cggcgcccgt cgtgtagaga atattgaaga attggtcgcc  660
caagctgaca tcgtaacagt aaacgcgcca ttgcacgccg gcacaaaggg tttgattaac  720
aaggagttac tgagcaaatt caaaaaagga gcttggcttg taaacactgc tcgcggcgca  780
atttgcgtag cagaagacgt cgctgctgcc ctggagtcag gacagttgcg cgggtatgga  840
ggtgacgtat ggttcccaca gccagctcct aaggatcacc cttggcgcga tatgcgtaac  900
aagtacggtg ctggaaacgc aatgacgcct cattattccg gtacgacgtt ggatgcacaa  960
actcgttatg cagagggcac aaaaaatatt ttggaatcct tttcacagg caagttcgac  1020
tatcgtcctc aagatatcat tctgcttaat ggggagtatg tgacaaaggc atacggtaag  1080
catgataaga aactcgagca ccatcaccat caccattga                         1119
```